(12) United States Patent
Ono

(10) Patent No.: US 7,525,668 B2
(45) Date of Patent: Apr. 28, 2009

(54) APPARATUS AND METHOD FOR APPEARANCE INSPECTION

(75) Inventor: Yuji Ono, Ehime (JP)

(73) Assignee: Panasonic Corporation, Osaka (JP)

( * ) Notice: Subject to any disclaimer, the term of this patent is extended or adjusted under 35 U.S.C. 154(b) by 144 days.

(21) Appl. No.: 11/793,016

(22) PCT Filed: Apr. 12, 2006

(86) PCT No.: PCT/JP2006/307722

§ 371 (c)(1),
(2), (4) Date: Jun. 14, 2007

(87) PCT Pub. No.: WO2006/112315

PCT Pub. Date: Oct. 26, 2006

(65) Prior Publication Data

US 2008/0225299 A1 Sep. 18, 2008

(30) Foreign Application Priority Data

Apr. 14, 2005 (JP) ............................. 2005-116869

(51) Int. Cl.
*G01B 11/24* (2006.01)
*G01N 21/86* (2006.01)

(52) U.S. Cl. .............. 356/601; 250/559.19; 250/559.22

(58) Field of Classification Search .................. None
See application file for complete search history.

(56) References Cited

U.S. PATENT DOCUMENTS

| 3,975,102 A | 8/1976 | Rosenfeld et al. |
| 4,689,491 A | 8/1987 | Lindow et al. |
| 5,841,539 A * | 11/1998 | Ikurumi et al. ............. 356/613 |
| 6,703,634 B2 * | 3/2004 | Ono ...................... 250/559.19 |

FOREIGN PATENT DOCUMENTS

| JP | 51-122462 | 10/1976 |
| JP | 62-245949 | 10/1987 |

(Continued)

OTHER PUBLICATIONS

Patent Cooperation Treaty (PCT) International Preliminary Report on Patentability, issued Oct. 16, 2007 in International Application No. PCT/JP2006/307722.

*Primary Examiner*—Michael P Stafira
(74) *Attorney, Agent, or Firm*—Wenderoth, Lind & Ponack, L.L.P.

(57) ABSTRACT

Rotating polygon mirrors are configured such that angles formed by a rotation axis and mirror surfaces differs from one another in the mirror surfaces in order to shift a collecting point of a scanning light flux in a sub-scanning direction in association with rotation at constant angular speed. A collecting point position forming optical system is configured such that the collecting point is moved in an inspection range Zr in a height direction Z. The XYZ scanning is performed by moving the inspection object in the sub-scanning direction such that the collecting point shifted in the sub-scanning direction and the height direction is linearly scanned in the height direction of the inspection object in synchronization with the rotation of the rotating polygon mirror at the constant angular speed, and the an appearance positional coordinate of the inspection object is determined by a confocal method to perform the appearance inspection.

7 Claims, 20 Drawing Sheets

FOREIGN PATENT DOCUMENTS

| | | |
|---|---|---|
| JP | 3-231105 | 10/1991 |
| JP | 5-40035 | 2/1993 |
| JP | 9-126739 | 5/1997 |
| JP | 9-257440 | 10/1997 |
| JP | 11-37723 | 2/1999 |
| JP | 2000-9422 | 1/2000 |

* cited by examiner

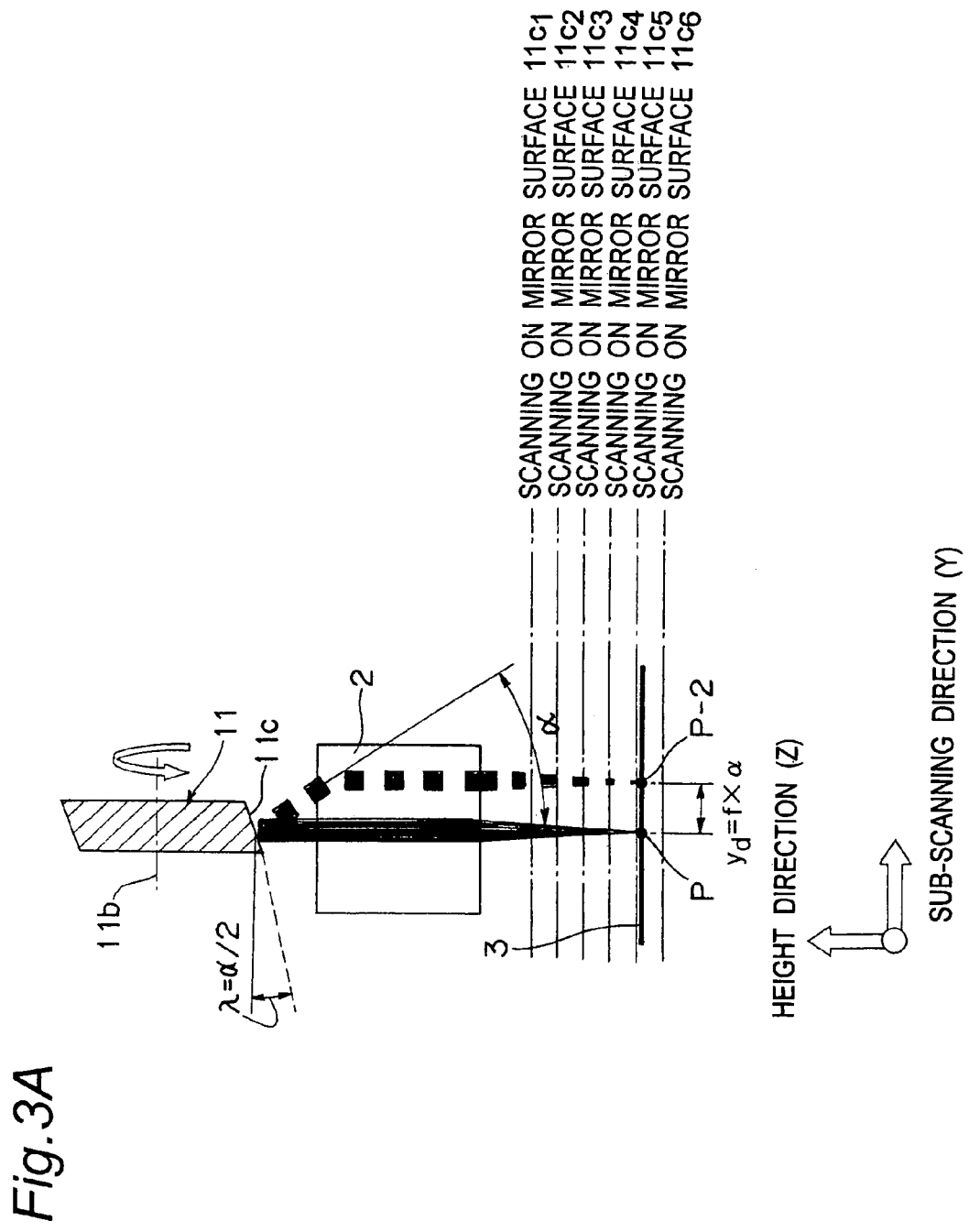

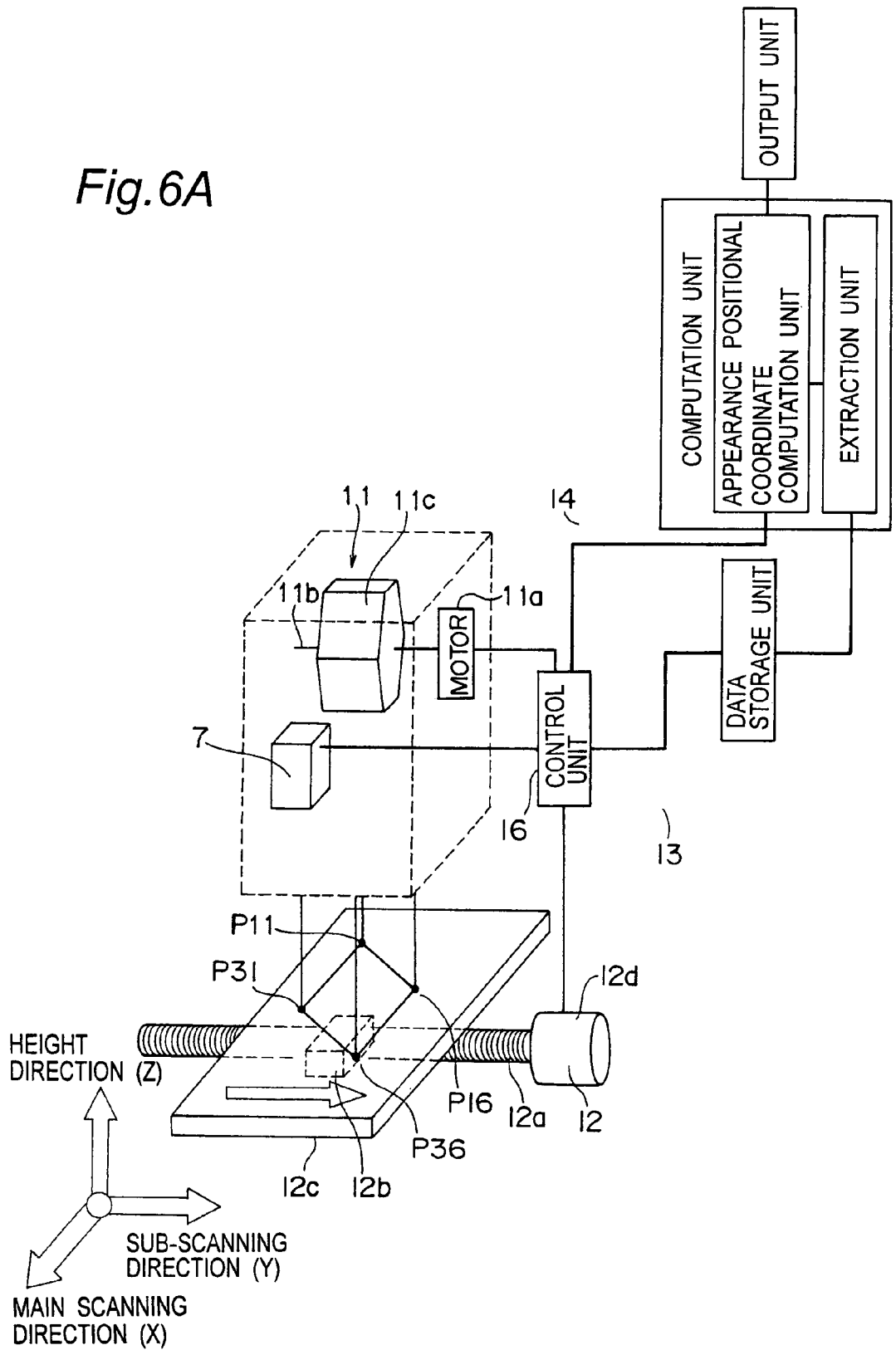

DOTTED LINE: IRRADIATION LIGHT,
SOLID LINE: REFLECTED
  LIGHT (REFERENCE),
BROKEN LINE: REFLECTED LIGHT
  (INSPECTION OBJECT MOVEMENT)

DOTTED LINE: IRRADIATION LIGHT,
SOLID LINE: REFLECTED LIGHT (REFERENCE),
BROKEN LINE: REFLECTED LIGHT (LENS MOVEMENT)

DOTTED LINE: IRRADIATION LIGHT,
SOLID LINE: REFLECTED LIGHT (REFERENCE),
BROKEN LINE: REFLECTED LIGHT (GLASS INSERTION)

$d_a = (1 - 1/n_n) \times t_a$

APPARATUS AND METHOD FOR APPEARANCE INSPECTION

TECHNICAL FIELD

The present invention relates to an apparatus and a method for appearance inspection of an inspection object. Particularly the present invention relates to the apparatus, in which the inspection object is irradiated with a spot light (irradiating light) such as a laser beam and is linearly scanned with a focal position forming optical system including a polygon mirror (hereinafter referred to as rotating polygon mirror) and a scanning collective lens, photoelectric conversion is performed from light intensity of reflected light (incident reflected light) which is reflected by the inspection object and deflected by a mirror surface rotating polygon mirror through the focal position forming optical system, and an appearance positional coordinate is determined to inspect an appearance of the inspection object by a principle of a confocal method.

Particularly, because a confocal relationship of the inspection object can be changed during a linear scanning operation performed by the rotation of the rotating polygon mirror in performing the appearance inspection of the inspection object at high speed, it is not necessary to move an optical system and the inspection object in a height direction, and the high-speed inspection of the inspection object can be realized with a simple configuration.

BACKGROUND ART

Conventionally, there are two main types of methods of geometrically measuring and inspecting a stereoscopic shape, i.e., a method of projecting various light beams to an object to measure and inspect the reflected light with a photodetector and a method in which the object is measured with a camera from plural directions under natural light of general illumination and the inspection is performed by determining the stereoscopic shape from a correlation among plural images.

The former is classified into various kinds by a light projection method, a type of the photodetector, a positional relationship thereof, and the like. In such classifications, as shown in FIG. 11A, there is a method in which a collecting light state of the reflected light by the confocal optical system is detected to search a focal position and thereby the inspection is performed by obtaining height information on the inspection object. In FIG. 11A, the irradiating light emitted from a light source 101 is emitted toward an inspection object 103, i.e., toward an irradiation direction as shown by a dotted line, a light separation mirror 104 transmits the irradiating light, and the irradiating light is collected at a collecting point Pa on the inspection object 103 by a collective lens 121. In the reflected light reflected by the collecting point Pa on a surface of the inspection object 103, the reflected light (incident reflected light) reflected toward an opposite direction to the irradiating direction is incident to the collective lens 121 again, the reflected light is reflected toward a direction orthogonal to the irradiating direction by a light separation mirror 104, and the reflected light is incident to a reflected light collective lens 105. Then, the reflected light passes through a micro hole of a shielding plate 106 while a collecting point Qa is formed in the micro hole of the shielding plate 106 by the reflected light collective lens 105, the reflected light is incident to a photodetector 107, and the photodetector 107 performs the photoelectric conversion of the light intensity into a photoelectric conversion signal output Ia. At this point, there is an optically confocal relationship between the collecting point Pa of the irradiating light collective lens 121 and the collecting point Qa of the reflected light collective lens 105 (that is, the micro hole of the shielding plate 106).

When the inspection object 103 is moved by a moving amount z from the irradiating light collecting point Pa toward the irradiating direction and located at a position of an inspection object 103-1, the reflected light reflected by the surface of the inspection object 103-1 is shown by a broken line, the reflected light collecting point is moved from the point Qa to a point Qa-1 which is close to the reflected light collective lens 105. Therefore, an image size of the reflected light is enlarged on the shielding plate 106, a quantity of the light passing through the micro hole of the shielding plate 106 is decreased in the reflected light collected by the reflected light collective lens 105, and the photoelectric conversion signal output Ia is decreased in the photodetector 107.

FIG. 11B shows a relationship between the moving amount za of the inspection object 103 and the photoelectric conversion signal output Ia of the photodetector 107. The photoelectric conversion signal output Ia becomes the maximum at the position of za=0 where a reflecting point of the inspection object 103 corresponds to the irradiating light collecting point Pa, and the photoelectric conversion signal output Ia becomes less at a position where the moving amount za is separated from zero. That is, the height information can be obtained at the irradiating light collecting point Pa of the inspection object 103 to perform the appearance inspection by moving the inspection object 103 in the irradiating direction or an opposite direction to the irradiating direction (hereinafter referred to as Z direction) to determine the moving amount za at which the photoelectric conversion signal output Ia becomes the maximum.

FIG. 11A shows an example of a method of moving only the inspection object 103. However, when the positions in the Z direction of the collecting point Pa of the irradiating light and the inspection object 103 are changed (hereinafter referred to as Z scanning), the same effect is obtained. It is clear that a method of moving the whole of the optical system while fixing the inspection object 103, which is of the Z scanning method, has the effect similar to the method of moving only the inspection object 103. FIGS. 12A and 12B show other Z scanning methods.

FIG. 12A shows a method in which the Z scanning is realized by moving only the irradiating light collective lens 121 in the optical system in the Z direction to move the irradiating light collecting point Pa to a point Pa-1. The method is useful in the case where the irradiating light incident to the irradiating light collective lens 121 is close to a parallel light. Only the irradiating light collective lens 121 is the moving body and the irradiating light collective lens 121 is usually light, so that high-speed measurement and simplified mechanism are achieved (for example, see Patent Document 1).

FIG. 12B shows a method in which an optical distance da between the irradiating light collective lens 121 and the inspection object 103 is changed by inserting parallel glass 110 having a thickness ta and a refractive index $n_n$ between the irradiating light collective lens 121 and the inspection object 103, and thereby the irradiating light collecting point Pa is moved to a point Pa-2 to realize the Z scanning. In the method, the plural pieces of parallel glass having the different thicknesses or refractive indexes are sequentially inserted between the irradiating light collective lens 121 and the inspection object 103, a disc in which the plural pieces of parallel glass are arranged is rotated at high speed, and thereby the high-speed Z scanning can be achieved (for example, see Patent Document 2).

Furthermore, there is a method, in which the reflected light from the inspection object 103 is branched into plural light beams by the plural light separation mirrors 104, the photoelectric conversion signal outputs Ia of branched reflected light beams are simultaneously measured to form the optical system equivalent to the Z scanning method by the plural shielding plates 106 and the plural photodetectors 107 which are placed at positions having different distances from the reflected light collective lens 105 in each branched reflected light, and thereby a time necessary for the Z scanning (for example, a time necessary to move the inspection object 103 and a time necessary to move the irradiating light collective lens 121) can be neglected to realize the high-speed Z scanning (for example, see Patent Document 3).

Thus, the height information on the inspection object 103 can be obtained at the irradiating light collecting point Pa by performing the Z scanning in the confocal method. Furthermore, the inspection object 103 is moved in an X direction and a Y direction which are orthogonal to the Z direction and orthogonal to each other, and the position of the irradiating light collecting point Pa is changed in the Y direction with respect to the inspection object 103 (hereinafter referred to as Y scanning) while the position of the irradiating light collecting point Pa is changed in the X direction with respect to the inspection object 103 (hereinafter referred to as X scanning), and thereby a stereoscopic coordinate (positional coordinate) of the inspection object 103 can be obtained to perform the appearance inspection (for example, see Patent Document 1). Similarly the positional coordinate of the inspection object 103 can be obtained to perform the appearance inspection, in the case where the inspection object 103 is fixed while the whole of the optical system is moved in the X direction and in the Y direction, or in the case where the inspection object 103 is moved in the X direction or in the Y direction while the whole of the optical system is moved in the X direction or in the Y direction.

One of means for achieving the high-speed X scanning and Y scanning is a method in which an optical system for scanning the irradiating light is newly provided in the above optical system to realize the X scanning and Y scanning (for example, see Patent Document 4). There is also a method in which multi-point simultaneous measurement is performed in an XY lattice manner by arranging many confocal optical systems including the light sources 101 to photodetectors 107 in the measuring optical system (for example, see Patent Document 5).

Patent Document 1: Japanese Unexamined Patent Publication No. S62-245949
Patent Document 2: Japanese Unexamined Patent Publication No. H9-126739
Patent Document 3: Japanese Unexamined Patent Publication No. H5-40035
Patent Document 4: Japanese Unexamined Patent Publication No. H3-231105
Patent Document 5: Japanese Unexamined Patent Publication No. H9-257440

DISCLOSURE OF THE INVENTION

Issue to be Improved by the Invention

However, in the conventional configuration, the XY scanning and the Z scanning are realized by the separated methods. Therefore, when the XY scanning and the Z scanning are simultaneously realized to achieve the speedup, the number of components is increased to complicate the structure, which results in issues such as cost increase, reliability decrease, and upsizing of apparatus.

In order to improved the conventional issues, an object of the present invention is to provide appearance inspection apparatus and method in which speedup of the appearance inspection is realized with a simple mechanism by incorporating the Z scanning mechanism into the XY scanning mechanism.

Means for Solving Issue

In order to achieve the above object, the present invention has the following constitutions.

According to a first aspect of the present invention, there is provided an appearance inspection apparatus characterized by comprising:

a light source for emitting a light flux;

a rotating polygon mirror which has at least three mirror surfaces in an outer peripheral portion thereof, is arranged to be rotatable about a rotation axis thereof at a constant angular speed, for deflecting the light flux emitted from the light source toward an inspection object by each of the mirror surfaces, so as to linearly scan the light flux in a main scanning direction by a rotation;

a collecting point position forming optical system for moving a collecting point in an inspection range in a height direction orthogonal to the main scanning direction of the inspection object while the light flux, deflected and scanned by each of the mirror surfaces of the rotating polygon mirror, is collected at the collecting point by the rotation of the rotating polygon mirror;

a photodetector for performing photoelectric conversion of light intensity of reflected light, which is reflected by the inspection object after passing through the collecting point position forming optical system and is deflected by the mirror surface of the rotating polygon mirror through the collecting point position forming optical system, into a photoelectric conversion signal output, the light intensity depending on a distance between the collecting point and a reflection point of the light flux on the inspection object;

an inspection object moving device for moving the inspection object in a sub-scanning direction orthogonal to both the main scanning direction and the height direction in synchronization with the rotation of the rotating polygon mirror at the constant angular speed; and a computation unit for determining an appearance positional coordinate of the inspection object to perform appearance inspection of the inspection object based on the photoelectric conversion signal output of the reflected light to which the photoelectric conversion is performed by the photodetector, wherein the rotating polygon mirror is configured such that mirror surface angles which are of angles formed between the mirror surfaces and the rotation axis of the rotating polygon mirror differ from one another in the mirror surfaces in order to shift the collecting point of the light flux in the sub-scanning direction in association with the rotation at the constant angular speed, and the inspection object moving device moves the inspection object in the sub-scanning direction in order to linearly scan the collecting point in the height direction of the inspection object during one revolution of the rotating polygon mirror at the constant angular speed, the collecting point being shifted in the sub-scanning direction by each of the mirror surfaces while moved in the inspection range in the height direction by the collecting point position forming optical system and, before the further one revolution at the constant angular speed is started by the rotating polygon mirror, the inspection object moving device moves the inspection object in the sub-scanning direction to perform the appearance inspection at a portion, different from a portion to which the appearance inspection is already performed during the one revolution of the rotating polygon mirror, on the inspection object by the linear scanning of the collecting point in the main scanning direction and the movement of the collecting point in the height direction in the inspection range.

According to a second aspect of the present invention, there is provided the appearance inspection apparatus as defined in the first aspect, characterized in that the collecting point position forming optical system includes a scanning collective lens which is arranged such that an optical axis thereof is inclined with respect to a direction orthogonal to the rotation axis of the rotating polygon mirror, for collecting the light flux deflected and scanned by each of the mirror surfaces of the rotating polygon mirror, at the collecting point which is moved in the inspection range in the height direction while linearly moved in the main scanning direction.

According to a third aspect of the present invention, there is provided the appearance inspection apparatus as defined in the first aspect, characterized in that the collecting point position forming optical system includes:

a scanning collective lens which is arranged such that an optical axis thereof is parallel to a direction orthogonal to the rotation axis of the rotating polygon mirror, for collecting the light flux deflected and scanned by each of the mirror surfaces of the rotating polygon mirror, at the collecting point; and a prism which is arranged between the scanning collective lens and the inspection object such that an incident plane thereof and an outgoing plane thereof are parallel to the main scanning direction, for deflecting the light flux incident from the incident plane and outputting the light flux from the outgoing plane, and the light flux passing through the scanning collective lens is incident from the incident plane of the prism, the light flux is deflected to be outputted from the outgoing plane, thereby collecting point is moved in the inspection range in the height direction while linearly moved in the main scanning direction.

According to a fourth aspect of the present invention, there is provided the appearance inspection apparatus as defined in the first aspect, characterized by further comprising a data storage unit in which the photoelectric conversion signal output of the reflected light is stored, the reflected light being outputted the photodetector during at least one revolution of the rotating polygon mirror, wherein the computation unit determines a position in the height direction of the inspection object to determine an appearance positional coordinate of the inspection object based on the photoelectric conversion signal output stored in the data storage unit, and to perform the appearance inspection of the inspection object.

According to a fifth aspect of the present invention, there is provided an appearance inspection method characterized by comprising:

rotating a rotating polygon mirror, which has at least three mirror surfaces in an outer peripheral portion and is configured such that mirror surface angles thereof formed by an rotation axis thereof and the mirror surfaces differ from one another in the mirror surfaces, about the rotation axis at a constant angular speed to linearly scan a light flux in a main scanning direction while the light flux is deflected toward an inspection object, the light flux being emitted from a light source to the mirror surface;

moving a collecting point in an inspection range in a height direction orthogonal to the main scanning direction of the inspection object while the light flux is collected at the collecting point using a collecting point position forming optical system in the deflection and scanning which are performed with the light flux by each of the mirror surfaces of the rotating polygon mirror;

moving the inspection object in a sub-scanning direction such that the collecting point is linearly scanned in the height direction of the inspection object, the collecting point being shifted in the sub-scanning direction orthogonal to the main scanning direction and the height direction by each of the mirror surfaces having different angles;

performing photoelectric conversion of light intensity of reflected light, reflected by the inspection object moved in the sub-scanning direction and deflected by the mirror surface of the rotating polygon mirror through the collecting point position forming optical system, into a photoelectric conversion signal output, the light intensity of the light flux depending on a distance between the collecting point and the reflection point of the light flux on the inspection object;

performing appearance inspection of the inspection object by determining an appearance positional coordinate of the inspection object based on the photoelectric conversion signal output;

moving the inspection object in the sub-scanning direction before further one revolution of the rotating polygon mirror at the constant angular speed is started; and performing the appearance inspection at a portion different from a portion to which the appearance inspection is already performed during one revolution of the rotating polygon mirror on the inspection object by the linear scanning of the collecting point in the main scanning direction and the movement of the collecting point in the height direction in the inspection range.

According to a sixth aspect of the present invention, there is provided the appearance inspection method as defined in the fifth aspect, characterized in that, in the deflection and scanning, the light flux, deflected and scanned by each of the mirror surfaces of the rotating polygon mirror, is collected at the collecting point by a scanning collective lens which constitutes the collecting point position forming optical system and of which an optical axis is arranged to be inclined with respect to a direction orthogonal to the rotation axis of the rotating polygon mirror, and the collecting point is collected so as to moved in the inspection range in the height direction while linearly moved in the main scanning direction.

According to a seventh aspect of the present invention, there is provided the appearance inspection method as defined in the fifth aspect, characterized in that, in the deflection and scanning, the light flux, deflected and scanned by each of the mirror surfaces of the rotating polygon mirror, is collected at the collecting point by a scanning collective lens which constitutes the collecting point position forming optical system and of which an optical axis is arranged to be parallel to a direction orthogonal to the rotation axis of the rotating polygon mirror; and the light flux passing through the scanning collective lens is incident from an incident plane of a prism and is deflected to be outputted from an outgoing plane of the prism, and the collecting point is collected so as to moved in the inspection range in the height direction while linearly moved in the main scanning direction, by the prism which constitutes the collecting point position forming optical system and is arranged between the scanning collective lens and the inspection object such that an incident plane and an outgoing plane are parallel to the main scanning direction.

EFFECT OF THE INVENTION

According to the first or fifth mode of the present invention, the mirror surface of the rotating polygon mirror is configured to have the different mirror surface angle which is of an angle formed between the rotation axis and the mirror surface such that the collecting point of the scanning light flux is shifted in the sub-scanning direction in association with the rotation at constant angular speed, the collecting point position forming optical system is configured such that the collecting point is moved in the inspection range in the height direction, the collecting point is moved in the inspection range in the height direction in synchronization with the rotation of the rotating polygon mirror at constant angular speed, and the inspection object is moved in the sub-scanning direction such that the collecting point shifted in the sub-scanning direction is linearly scanned in the height direction of the inspection object. Therefore, during the rotating operation of the rotating polygon mirror, the scanning (X scanning) can be performed in the main scanning direction with respect to the inspection object by one mirror surface, the scanning (Z scanning) can be performed in the height direction with respect to the inspection object by changing the mirror surfaces having the different mirror surface angles in one revolution of the rotating polygon mirror, and the scanning (Y scanning) can be performed in the sub-scanning direction with respect to the inspection object by performing the plural revolutions of the rotating polygon mirror while moving the inspection object in the sub-scanning direction. That is, the Z scanning can be incorporated into the XY scanning mechanism, and the high-speed appearance inspection can be realized with the simple mechanism as described above.

In the case where the appearance inspection is performed to the inspection object by the first mode of the present invention, the computation unit can perform the stereoscopic appearance inspection of the inspection object by determining the total of (2×2×3=) 12 appearance positional coordinates of the inspection object, i.e., the two appearance positional coordinates in the main scanning direction (although at least two appearance positional coordinates are required to determine the stereoscopic positional coordinate of the appearance, at least three appearance positional coordinates are required to enhance the X resolution), two appearance positional coordinates in the sub-scanning direction (although at least two appearance positional coordinates are required to determine the stereoscopic positional coordinate of the appearance, at least three appearance positional coordinates are required to enhance the Y resolution), and three appearance positional coordinates in the height direction (at least three appearance positional coordinates, depending on the number of mirror surfaces of the rotating polygon mirror).

On the contrary, in Patent Document 1, in addition to the drive mechanism for performing the XY scanning, the drive mechanism for moving the irradiating light collective lens in the height direction (Z direction) is required to perform the Z scanning, and there is a risk of generating vibration in the stop of the irradiating light collective lens to decrease the inspection accuracy when the irradiating light collective lens is moved in the height direction. According to the first or fifth mode of the present invention, the drive mechanism for moving the irradiating light collective lens and the like in the height direction is not required, so that the decrease in inspection accuracy can be prevented. In Patent Document 3, it is necessary that the plural light separation mirrors, the plural shielding plates, and the plural photodetectors be arranged in order to perform the Z scanning. According to the first or fifth mode of the present invention, it is necessary to arrange the one light separation mirror, the one shielding plate, and the one photodetector, so that the increase in the number of components can be suppressed, and the cost increase and the upsizing of the apparatus can be prevented.

BRIEF DESCRIPTION OF DRAWINGS

These and other aspects and features of the present invention will become clear from the following description taken in conjunction with the preferred embodiments thereof with reference to the accompanying drawings, in which:

FIG. 3A is a view explaining a mirror surface angle effect of a rotating polygon mirror of the appearance inspection apparatus and method according to the first embodiment of the present invention;

FIG. 6A is a perspective view schematically showing a configuration for explaining sub-scanning direction feeding operation and data processing in the appearance inspection apparatus according to the first embodiment of the present invention;

BEST MODE FOR CARRYING OUT THE INVENTION

Figure 1A:
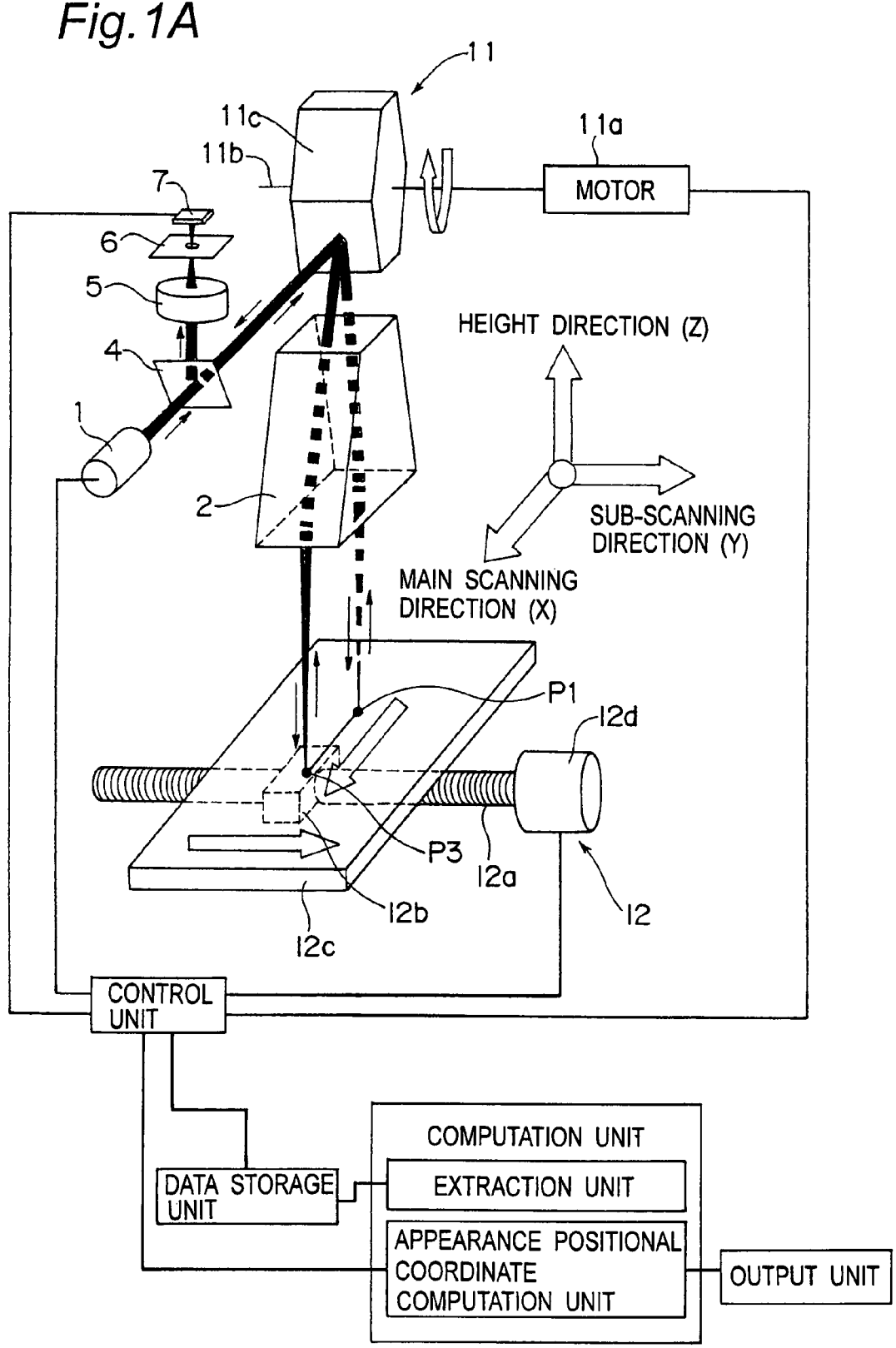
FIG. 1A is a perspective view schematically showing a configuration of an optical system and a mechanical system of an appearance inspection apparatus according to a first embodiment of the present invention.

Before the description of the present invention proceeds, it is to be noted that like parts are designated by like reference numerals throughout the accompanying drawings.

Hereinbelow, an appearance inspection apparatus and method according to embodiments of the present invention will be described in detail with reference to the accompanying drawings.

FIRST EMBODIMENT

Figure 1B:
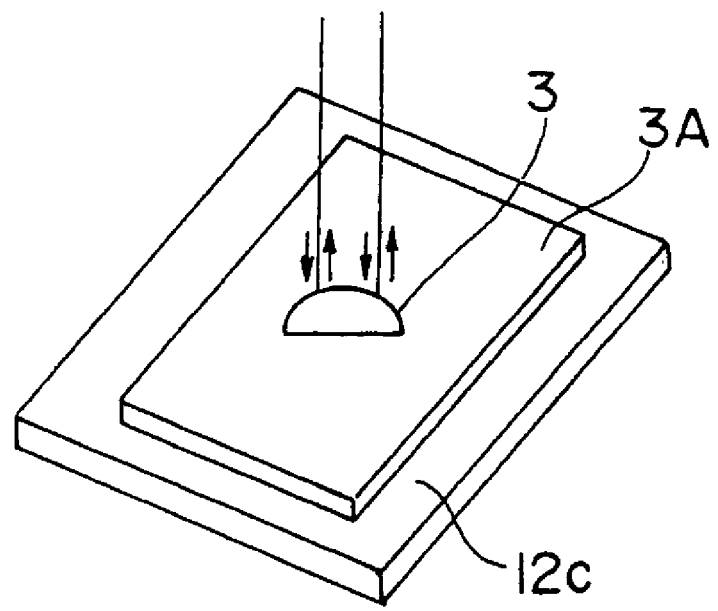
FIG. 1B is a partially enlarged perspective view of FIG. 1A.
Figure 2:
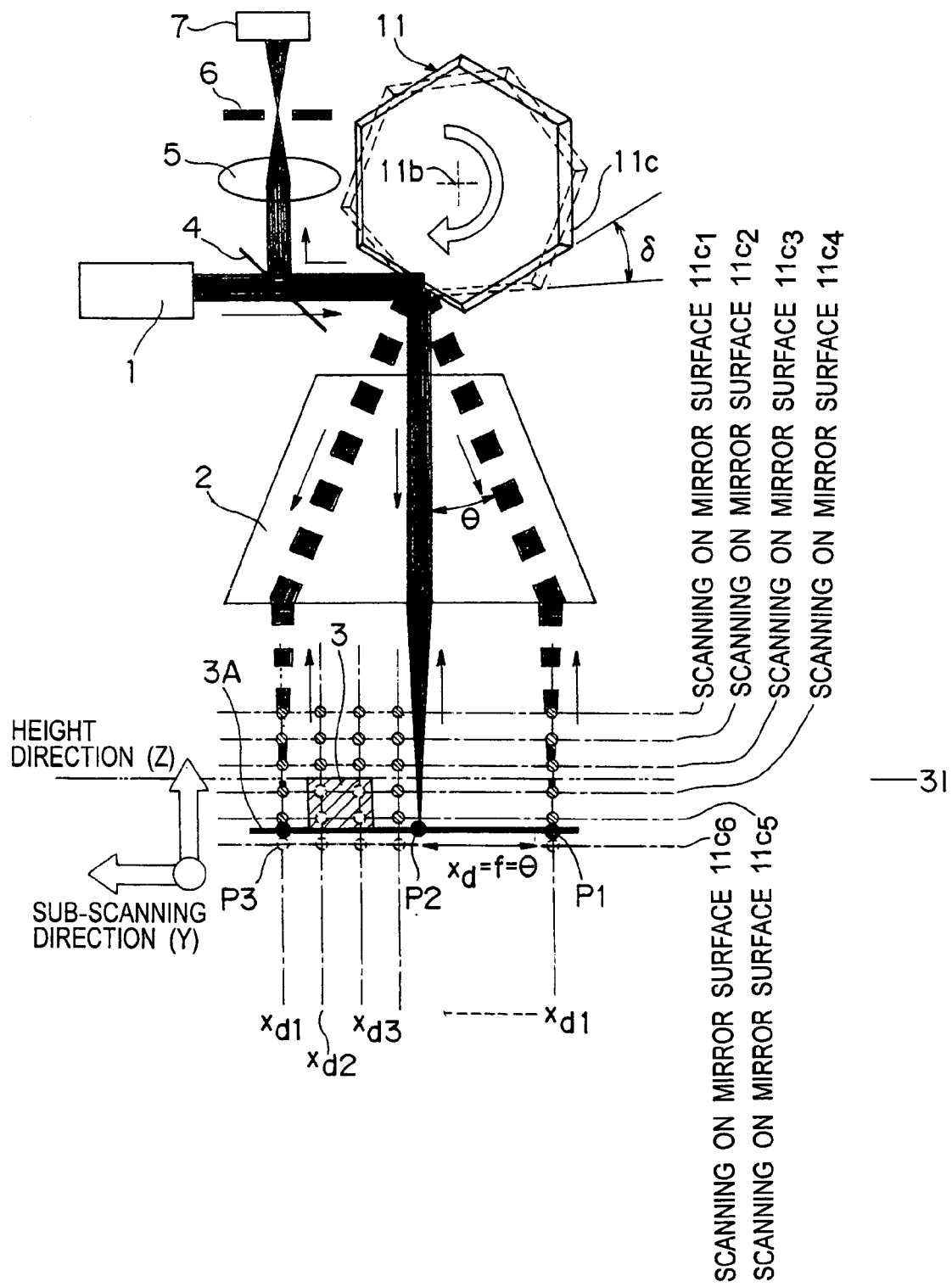
FIG. 2 is a schematic view showing the configuration of the optical system of the appearance inspection apparatus and method according to the first embodiment of the present invention when viewed from a sub-scanning direction.

FIG. 1A is a perspective view schematically showing a configuration of an optical system and a mechanical system of an appearance inspection apparatus according to a first embodiment of the present invention, and FIG. 1B is a partially enlarged perspective view of FIG. 1A showing an inspection object 3. FIG. 2 is a schematic view showing the optical system when viewed from the sub-scanning direction.

A basic configuration of the appearance inspection apparatus according to the first embodiment of the present invention will be described with reference to FIGS. 1A and 1B. The appearance inspection apparatus according to the first embodiment of the present invention includes a light source 1, a rotating polygon mirror 11, a motor 11a, a scanning collective lens 2 which constitutes an example of collecting point position forming optical system, a light separation mirror 4, a reflected light collective lens 5, a shielding plate 6, a photodetector 7, a table feeding device 12 which is of an example of the inspection object moving device, a data storage unit 13 which is of an example of the storage unit, a computation unit 14, an output unit 15, and a control unit 16.

The light source 1 emits the light flux such as the laser beam which is of the irradiating light to the rotating polygon mirror 11. The rotating polygon mirror 11 is formed in a polygon prism (for example, hexagonal prism). The rotating polygon mirror 11 has plural mirror surfaces 11c (reflection planes) in an outer peripheral portion thereof, and the mirror surfaces 11c have different mirror surface angles. The rotating polygon mirror 11 is formed to be rotatable in one direction at a constant angular speed by the motor 11a. In the rotating polygon mirror 11, each mirror surface 11c is formed to be able to deflect the irradiating light from the light source 1 toward the inspection object 3 (for example, an electronic component mounted on a board or solder paste for connecting the board and the electronic component) in a direction (downward direction in the vertical direction of FIG. 1) opposite a height direction Z (upward direction in the vertical direction of FIG. 1). The scanning collective lens 2 is arranged between the rotating polygon mirror 11 and the inspection object 3, and the scanning collective lens 2 collects the irradiating light deflected by the rotating polygon mirror 11 to a point P located near an upper surface of the inspection object 3 (hereinafter the collecting point in which the irradiating light deflected by the rotating polygon mirror 11 is collected by the scanning collective lens 2 is referred to as irradiating light collecting point).

The light separation mirror 4 having a rectangular plate shape is arranged between the light source 1 and the rotating polygon mirror 11. The irradiation light is collected to the point located near the upper surface of the inspection object 3 by the scanning collective lens 2, and the irradiation light is reflected from the inspection object 3 toward the height direction Z. The reflected light which proceeds through a path opposite the irradiating light to return to the light source 1 is separated from the irradiating light of the light source 1 and caused to be incident to the disc-shape reflected light collective lens 5 by the light separation mirror 4, namely, the reflected light is caused to run out from the irradiation path of the irradiating light of the light source 1 to be incident to the reflected light collective lens 5 by the light separation mirror 4. The reflected light collective lens 5 collects the reflected light separated by the light separation mirror 4 to a neighborhood near a micro hole made in the shielding plate 6 having the rectangular plate shape. The reflected light is incident to the photodetector 7 by passing through the micro hole of the shielding plate 6, and the photodetector 7 performs photoelectric conversion of light intensity of the reflected light into a photoelectric conversion signal output I.

The table feeding device 12 includes a drive shaft 12a, a nut member 12b, a table 12c, and a drive motor 12d. The drive shaft 12a is arranged so as to extending in a sub-scanning direction Y which is orthogonal to both a height direction Z and a main scanning direction X. The nut member 12b is screwed on the drive shaft 12a, and the nut member 12b can be traveled on the drive shaft 12a by normally and reversely rotating the drive shaft 12a. The table 12c having the rectangular plate shape is fixed to the nut member 12b, and the table 12c can hold a board 3A on which the inspection object 3 is placed. The drive motor 12d normally and reversely rotate the drive shaft 12a. In the table feeding device 12, the drive motor 12d is driven by the control unit 16 to normally and reversely rotates the drive shaft 12a, and the nut member 12b and the table 12c fixed thereto are traveled in the Y direction. Therefore, the inspection object 3 can be traveled in the Y direction.

The control unit 16 is connected to the light source 1, the photodetector 7, the motor 11a, the drive motor 12d, and the data storage unit 13, and the control unit 16 controls the drive of each of the light source 1, the photodetector 7, the motor 11a, and the drive motor 12d based on an operating program previously stored in the data storage unit 13. The operating program of each device is stored in the data storage unit 13, and the reflected-light photoelectric conversion signal output I which is outputted after the photoelectric conversion by the photodetector 7 is also stored in the data storage unit 13. The computation unit 14 includes an extraction unit 14a connected to the data storage unit 13 and an appearance positional coordinate computation unit 14b connected to the extraction unit 14a. The computation unit 14 determines a positional coordinate of an appearance of the inspection object 3 based on the reflected-light photoelectric conversion signal output I stored in the data storage unit 13. For example, the output unit 15 is formed by a display. The output unit 15 is connected to the appearance positional coordinate computation unit 14b, and the output unit 15 outputs and displays the positional coordinate of the appearance of the inspection object 3 computed by the appearance positional coordinate computation unit 14b.

Thus, the appearance inspection apparatus of the first embodiment of the present invention has the above basic configuration. The detailed configuration of the appearance inspection apparatus of the first embodiment of the present invention will be described below along with the operation.

Referring to FIGS. 1A, 1B, and 2, the control unit 16 controls the drive to cause the light source 1 to emit the light flux. The light flux which is emitted as the irradiating light from the light source 1 is deflected by one mirror surface 11c of the rotating polygon mirror (polygon mirror) 11. Then, the light flux is incident to the scanning collective lens 2, and the light flux is outputted as the collective light flux to become the scanning light flux which is collected at the point P near the surface of the inspection object 3. In the light flux emitted from the light source 1, an angle of the scanning light flux incident to the scanning collective lens 2 is changed by rotating the rotating polygon mirror 11 whose drive is controlled by the control unit 16, and the irradiating light collecting point P is continuously moved from a point P1, a point P2, to a point P3 to perform linearly scanning in the main scanning direction X to the inspection object 3 (hereinafter referred to as X scanning). In the light reflected from the inspection object 3 in the light with which is irradiated the inspection object 3, the reflected light (incident reflected light) in the height direction Z (also referred to as scanning light flux direction) passes through the scanning collective lens 2 to proceed through the path opposite the scanning light flux to the rotating polygon mirror 11, the reflected light is separated from the scanning light flux by the light separation mirror 4, and then the reflected light reaches the photodetector 7 through the confocal optical system (reflected light collective lens 5 and shielding plate 6) similar to the conventional example. Thus, the photoelectric conversion signal output I can be obtained with the photodetector 7 from the light intensity of the incident reflected light on the scanning line of the inspection object 3 by rotating the rotating polygon mirror 11.

At this point, the control unit 16 controls the drive of the drive motor 12d of the table feeding device 12 in synchronization with the rotation of the rotating polygon mirror 11 to move the inspection object 3 held on the table 12c in the direction (hereinafter referred to as sub-scanning direction Y) which is orthogonal to both the main scanning direction X and the height direction Z. An f–θ lens is usually used as the scanning collective lens 2, in order that the rotating speed of the rotating polygon mirror 11 is usually kept constant while the moving speed (scanning speed) of the scanning light flux is kept constant in the main scanning direction X. In the f–θ lens, as shown in FIG. 2, a relationship between a change angle θ of an incident angle (which is double a change angle δ of a deflection angle by the rotating polygon mirror 11) and a scanning position change $x_d$ becomes linear proportion ($x_d$=f×θ: referred to as f–θ characteristic) in which a focal distance f is a proportional coefficient. In the first embodiment the f–θ lens is used as the scanning collective lens 2. In FIG. 2, the point P2 is substantially located in the middle of the points P1 and P3 by way of example. However, the point P2 shall be located at an arbitrary position on the scanning range of from the point P1 to the point P3.

Figure 3B:
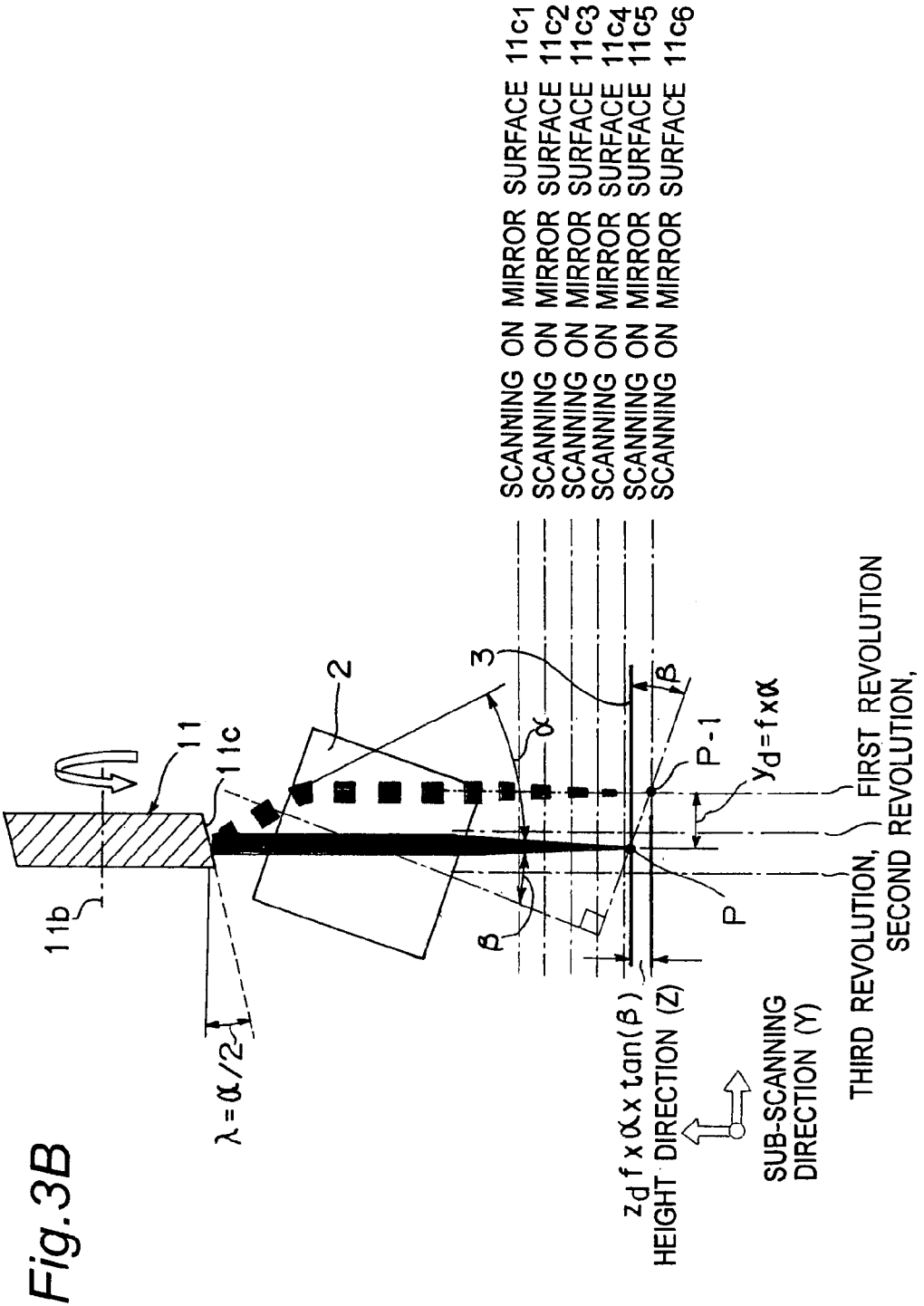
FIG. 3B is a view explaining an installation angle effect of a scanning collective lens of the appearance inspection apparatus and method according to the first embodiment of the present invention.

FIGS. 3A and 3B are views showing the optical system of the first embodiment of the present invention when viewed from the main scanning direction X, and explain the effect by the optical system.

In FIG. 3A, in the case where an angle λ (hereinafter referred to as mirror surface angle λ) formed by a mirror surface 11c of the rotating polygon mirror 11 and a rotation axis 11b of the rotating polygon mirror 11 is λ=α/2, an angle formed by a plane perpendicular to the rotation axis 11b of the rotating polygon mirror 11 and the light flux of the light source 1 deflected by a reflection plane of the rotating polygon mirror 11 becomes α. As a result, as shown by a dotted line in FIG. 3A, the collecting position of the scanning light flux becomes a point P–2 in the inspection object 3 which is shifted by $y_d$=f×α in the sub-scanning direction Y due to the fθ characteristic of the scanning collective lens 2 with respect to the irradiating light collecting point P in the case of α=0. In the case where an angle formed by an optical axis of the scanning collective lens 2 and a plane orthogonal to rotation axis 11b of the rotating polygon mirror 11 is β as shown in FIG. 3B, because an angle formed by the collecting plane of the scanning collective lens 2 and the rotation axis 11b of the rotating polygon mirror 11 becomes β, the irradiating light collecting point of the scanning light flux becomes a point P–1 which is shifted by $y_d$=f×α in the sub-scanning direction Y and by $z_d$=f×α×tan(β) in the height direction Z with respect to the irradiating light collecting point P in the case of α=β=0. The shift $z_d$ in the height direction Z becomes substantially constant in any main scanning direction position $x_{dj}$, because the mirror surface angle λ of the rotating polygon mirror 11 is substantially kept constant in performing the scanning with the same mirror surface 11c even if the rotation angle of the rotating polygon mirror 11 is changed. That is, in the optical system having the above configuration, the whole of the scanning line formed by a locus of the irradiating light collecting point P of the scanning light flux can be shifted in the height direction Z with respect to the inspection object 3 by the mirror surface angle λ of the rotating polygon mirror 11.

Figure 4A:
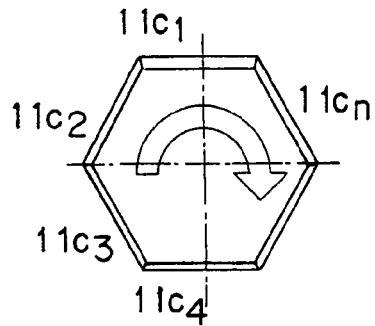
FIG. 4A is a side view showing a mirror surface angle change of the rotating polygon mirror of the appearance inspection apparatus according to the first embodiment of the present invention.
Figure 4B:
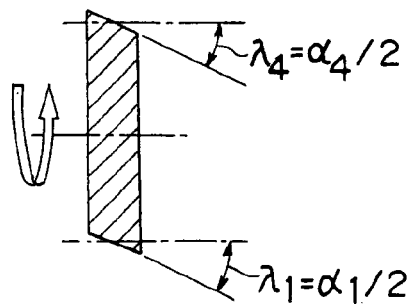
FIG. 4B is a sectional view showing the mirror surface angle change of the rotating polygon mirror of the appearance inspection apparatus according to the first embodiment of the present invention.
Figure 4C:
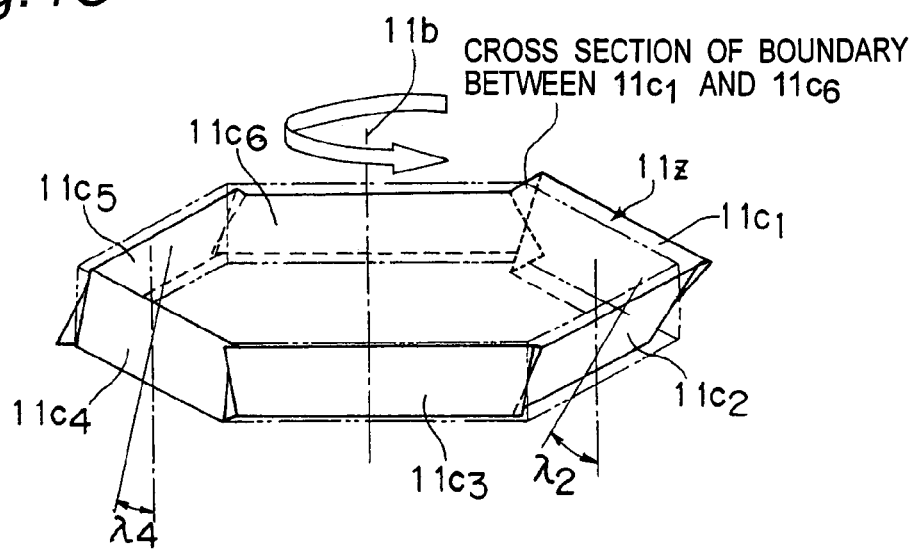
FIG. 4C is a perspective view showing a shape example of the rotating polygon mirror of the appearance inspection apparatus according to the first embodiment of the present invention.

FIGS. 4A to 4C show the effect of the rotating polygon mirror 11 when each mirror surface angle λ is changed. As shown in FIG. 4A, when the mirror surface angle λ of the rotating polygon mirror 11 having n mirror surfaces 11c is changed in each mirror surface 11c, a height direction position $z_{di}$ of the irradiating light collecting point P can be changed n times during one revolution of the rotating polygon mirror 11. That is, the sub-scanning direction position $y_{di}$ and height direction position $z_{di}$ of the scanning line formed by a first mirror surface $11c_i$ (i is an arbitrary number of the n mirror surface numbers and i is an integer of 1 to n) having a mirror surface angle $\lambda_i$ $(=\alpha_i/2)$ become $y_{di}=f\times\alpha_i$ and $z_{di}=f\times\alpha_i\times\tan(\beta)$ respectively, and the sub-scanning direction position $y_{di}$ and the height direction position $z_{di}$ are changed n times (i=1 to n) by one revolution of the rotating polygon mirror 11. Therefore, the X scanning and the YZ scanning can simultaneously be performed to the inspection object 3 by rotating the rotating polygon mirror 11.

FIG. 4C shows a shape example of the rotating polygon mirror 11. FIG. 4C is a perspective view showing the rotating polygon mirror 11 having the six mirror surfaces (in other words, the mirror surface number i is 1 to 6) in the case where each mirror surface angle $\lambda_i$ $(=\alpha_i/2)$ is increased in proportion to the mirror surface number i. FIG. 4C also shows the case where all the mirror surface angles λ of the rotating polygon mirror 11z become zero (namely, the hexagonal prism is obtained because all the mirror surface angles λ are parallel to the rotation axis) as a comparative example by an alternate long and two short dashes line. As shown in FIG. 4C, in the rotating polygon mirror 11, the angle of the mirror surface 11c is gradually changed from the first mirror surface $11c_i$ to the sixth mirror surface $11c_6$. In FIG. 4C, the first mirror surface $11c_1$ to the third mirror surface $11c_3$ are orientated downward, and the fourth mirror surface $11c_4$ to the sixth mirror surface $11c_6$ are orientated upward. Because each mirror surface 11c is formed in the flat surface, there is a cross section in which two triangles are combined in a boundary with an adjacent mirror surface. Particularly an angle difference between the first mirror surface $11c_1$ and the sixth mirror surface $11c_6$ becomes the maximum, so that the cross section of the boundary also becomes the maximum. That is, assuming that dλ is the angle difference between the mirror surfaces adjacent to each other except for the angle difference between the first mirror surface $11c_1$ and the sixth mirror surface $11c_6$, each mirror surface angle $\lambda_i$ is expressed by the following equation.

$$\lambda_i=(i-3.5)\times d\lambda$$

where i is a mirror surface number which is of an integer ranging from 1 to 6, the mirror surface angle $\lambda_1$ of the first mirror surface $11c_1$ becomes $-2.5\times d\lambda$, the mirror surface angle $\lambda_6$ of the sixth mirror surface $11c_6$ becomes $2.5\times d\lambda$, and the angle difference between the first mirror surface $11c_1$ and the sixth mirror surface $11c_6$ becomes $-5\times d\lambda$.

In the following description, unless otherwise noted, it is assumed that the rotating polygon mirror 11 is formed in the shape (the number of mirror surfaces is six and an angle difference dλ between the mirror surfaces adjacent to each other is constant) shown in FIG. 4C. At least three surfaces are required for the number of mirror surfaces of the rotating polygon mirror 11. Preferably appearance inspection accuracy is improved as the number of mirror surfaces is increased, because the number of positional coordinate samples for shifting the irradiating light collecting point P in the main scanning direction X to perform the appearance inspection to the inspection object 3 can be increased as the number of mirror surfaces is increased. In the first embodiment, the rotating polygon mirror 11 is configured such that the angle of the mirror surface 11c is gradually changed from the first mirror surface $11c_1$ to the sixth mirror surface $11c_6$, e.g., such that the angle of the mirror surface 11c is changed from +1°, +0.5°, 0°, −0.5°, to −1°. However, the present invention is not limited to the first embodiment. For example, the same effect as the first embodiment can be obtained when the rotating polygon mirror 11 is configured such that the angle of the mirror surface 11c is randomly changed from +1°, −0.5°, 0°, −1°, to +0.5°.

Figure 5A:
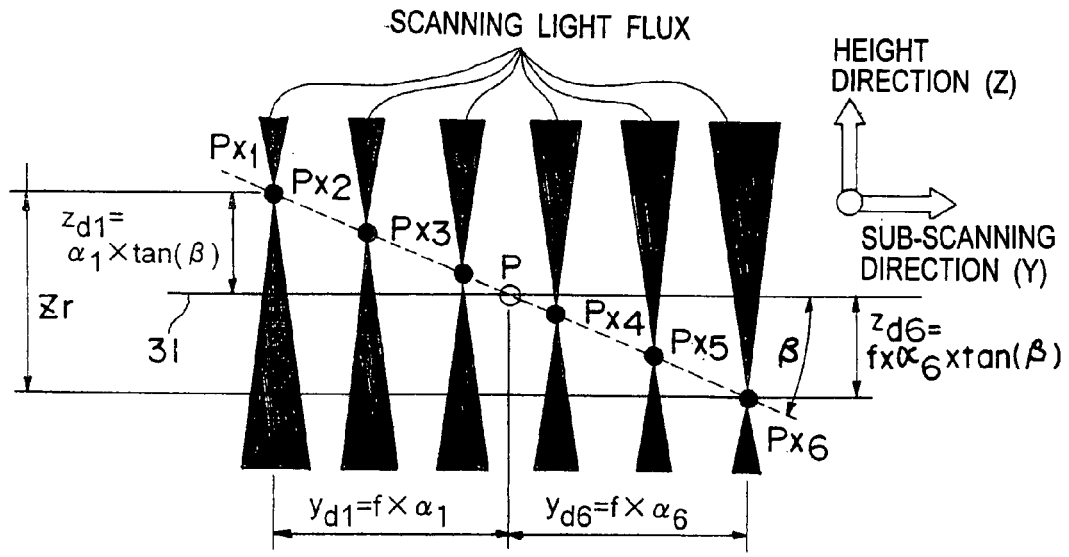
FIG. 5A is a side view showing a change by a mirror surface at an irradiating light collecting point of the appearance inspection apparatus and method according to the first embodiment of the present invention.

The detailed state of the YZ scanning of the scanning line, generated by rotating the rotating polygon mirror 11, will be described below with reference to FIGS. 5A and 5B. FIG. 5A is a view showing the YZ scanning state of the scanning line when viewed from the main scanning direction X like FIG. 3B. In this case, the control unit 16 controls the rotating drive of the rotating polygon mirror 11 such that the deflecting operation of the light flux of the light source 1 is started from the first mirror surface $11c_1$. The rotating polygon mirror 11 deflects the light flux of the light source 1 in the order from the first mirror surface $11c_1$ to the sixth mirror surface $11c_6$ by one revolution of the rotating polygon mirror 11.

When the mirror surface 11c of the rotating polygon mirror 11 which deflects the light flux of the light source 1 is changed from the first mirror surface $11c_1$ to the sixth mirror surface $11c_6$ by the rotating operation of the rotating polygon mirror 11, the position of the irradiating light collecting point is changed five times from a point $Px_1$ to a point $Px_6$ (the point P shown in FIG. 5A is the irradiating light collecting point in the case where the mirror surface angle λ is 0°, namely, the mirror surface 11c of the rotating polygon mirror 11 is parallel to the rotation axis 11b). The points $Px_1$ to $Px_6$ and the point P are located on a plane which has the angle β with respect to the plane 31 perpendicular to the scanning light flux, and the point P becomes a nodal point with the plane 31. The plane 31 is a plane (virtual inspection reference plane) passing through a midpoint of an inspection range Zr in the height direction Z, and the inspection range Zr is previously set to the inspection object 3. In order to inspect the whole inspection object 3, preferably the inspection range Zr in the height direction Z is set in the range of from the position higher than the uppermost portion of the inspection object 3 to the position equal to or lower than the lowermost portion of the inspection object 3. As shown in FIG. 4C, because the mirror surface angle $\lambda_i$ of the rotating polygon mirror 11 is increased in proportion with the mirror surface number i, the sub-scanning direction position $y_{di}$ and height direction position $z_{di}$ of each irradiating light collecting point are obtained with respect to the point P by the following equations.

$$y_{di}=f\times\alpha_i=(i-3.5)\times f\times d\alpha$$

$$z_{di}=f\times\alpha_i\times\tan(\beta)=(i-3.5)\times f\times d\alpha\times\tan(\beta)$$

Due to a constant value of $d\alpha=2\times d\lambda$, the sub-scanning direction position $y_{di}$ and height direction position $z_{di}$ of each irradiating light collecting point are changed in proportion with the mirror surface number i, and a change interval is constant. The change interval becomes $f\times d\alpha$ in the sub-scanning direction Y, and the change interval becomes $f\times d\alpha\times\tan(\beta)$ in the height direction Z.

Figure 5B:
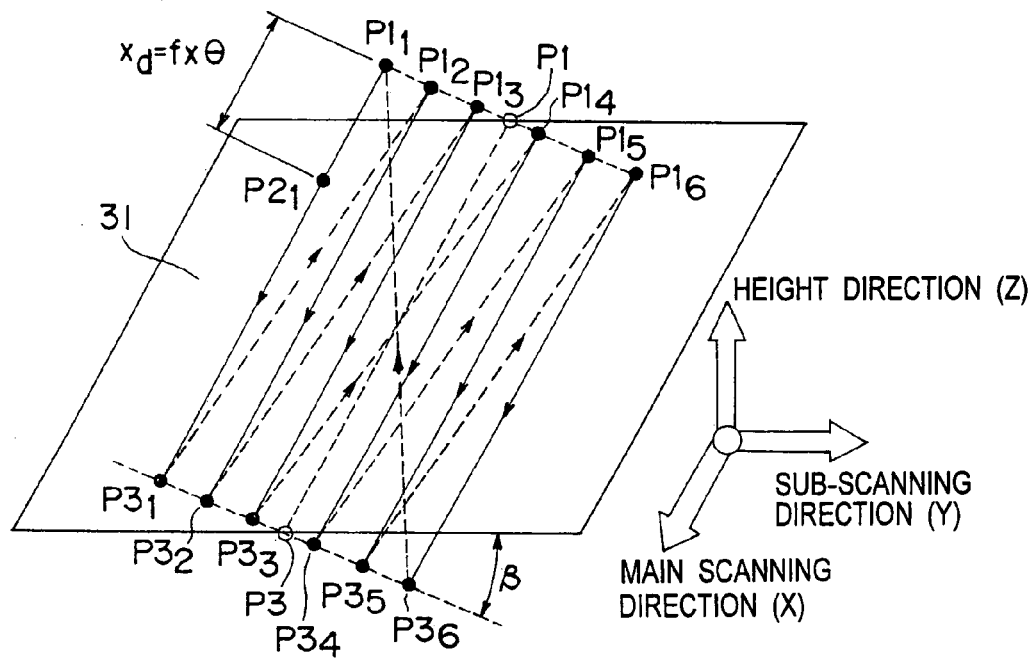
FIG. 5B is a perspective view showing the change by the mirror surface at the irradiating light collecting point of the appearance inspection apparatus and method according to the first embodiment of the present invention.

FIG. 5B is a perspective view showing the state similar to that of FIG. 5A. However, in order to illustrate the linear scanning operation performed by the rotating operation of the rotating polygon mirror 11, the irradiating light collecting point is set at $P1_i$ at the start of the scanning and the irradiating light collecting point is set at $P3_i$ at the end of the scanning (i is a surface number ranging from 1 to 6). That is, the point $Px_1$ of FIG. 5A indicates the whole locus of the irradiating light collecting point in the linear scanning between the points $P1_1$ to $P3_1$ in FIG. 5B, and the same holds for the points $Px_2$ to $Px_6$ (however, as described above, the point P indicates the locus of the irradiating light collecting point of the linear scanning of the points P1 to P3).

A temporal change in position of the irradiating light collecting point, generated by the rotation of the rotating polygon mirror 11, will be described below. When the reflection of the light flux of the light source 1 from the first mirror surface $11c_1$ is started by the rotation of the rotating polygon mirror 11, the scanning is started at the point $P1_1$, and the linear scanning is performed up to the point $P3_1$. Then, when the reflection plane of the light flux of the light source 1 is changed to the first mirror surface $11c_2$ by the rotation of the rotating polygon mirror 11, the scanning is started at the point $P1_2$, and the linear scanning is performed up to the point $P3_2$. Then, when the reflection plane of the light flux of the light source 1 is changed to the third mirror surface $11c_3$ to fourth mirror surface $11c_6$ by the rotation of the rotating polygon mirror 11, the irradiating light collecting point is also changed from the point $P1_3$ to the point $P3_3$, from the point $P1_4$ to the point $P3_4$, from the point $P1_5$ to the point $P3_5$, and from the point $P1_6$ to the point $P3_6$. In FIG. 5B, solid-line arrows from the point $P1_3$ to the point $P3_3$, from the point $P1_4$ to the point $P3_4$, and from the point $P1_5$ to the point $P3_5$ show the linear scanning by the movement of the irradiating light collecting point. In FIG. 5B, dotted-line arrows between the point $P3_3$ and the point $P1_4$, between the point $P3_4$ and the point $P1_5$, and between the point $P3_5$ and the point $P1_6$ show the state in which the irradiating light collecting point does not exist, i.e., the state in which the linear scanning is not performed. When the reflection plane of the light flux of the light source 1 is changed from the sixth mirror surface $11c_1$ to the first mirror surface $11c_6$ by the rotation of the rotating polygon mirror 11, the light flux of the light source 1 is reflected by the first mirror surface $11c_1$ to start the scanning again. Then, the irradiating light collecting point is changed from the point $P3_6$, the point $P1_1$, the point $P3_1$, the point $P1_2$ . . . , and the same operation is repeated from start of the scanning start at the point $P1_1$. Thus, the irradiating light collecting point is moved from the point $P1_1$ to the point $P3_6$ by the one revolution of the rotating polygon mirror 11, and the irradiating light collecting point repeatedly scans the same path from the point $P1_1$ to the point $P3_6$ by the continuous rotation of the rotating polygon mirror 11.

When the change angle δ of the deflection angle of the mirror surface 11c of the rotating polygon mirror 11 is changed by further rotating the rotating polygon mirror 11 from the state in which the rotating polygon mirror 11 is located at the irradiating light collecting point $P1_1$ which is of the scanning start point, namely when the irradiating light collecting point becomes irradiating light collecting point $P2_1$ by changing the position on the same mirror surface 11c where the light flux of the lightsource 1 is reflected by the rotating polygon mirror 11, the change interval (for example, distance from the point $P1_1$ to the point $P1_2$) $x_d$ in the main scanning direction X becomes $x_d = f \times 2 \times \delta = f \times \theta$ due to the f–θ characteristics of the scanning collective lens 2. The letter θ designates a change angle of the incident angle and θ=2×δ.

As described above, the angles λ of the mirror surfaces 11c of the rotating polygon mirror 11 are formed so as to be different by one another as shown in FIG. 4C. Therefore, the main scanning direction position $x_{dj}$ of the irradiating light collecting point is changed to perform the linear scanning (X scanning) by reflecting the light flux of the light source 1 from one mirror surface 11c, and the sub-scanning direction position $y_{di}$ and the height direction position $z_{di}$ can be changed to simultaneously perform the two scannings (YZ scanning) by rotating the rotating polygon mirror 11 to switch the mirror surfaces 11c which reflect the light flux of the light source 1.

Figure 6B:
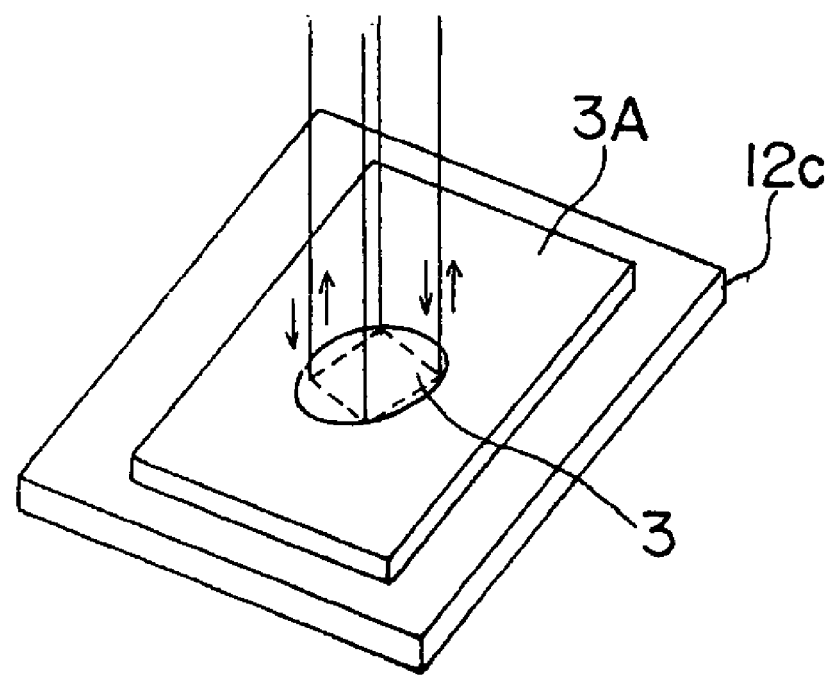
FIG. 6B is a partially enlarged view of FIG. 6A.

Then, a feeding operation in the sub-scanning direction Y of the inspection object 3 and data processing in the appearance inspection apparatus of the first embodiment of the present invention will be described with reference to FIGS. 6A and 6B. FIG. 6A is a perspective view schematically showing the configuration for explaining the sub-scanning direction feeding operation of the inspection object 3 and the data processing in the appearance inspection apparatus of the first embodiment of the present invention, and FIG. 6B is a partially enlarged view of FIG. 6A showing the inspection object 3.

The control unit 16 controls the drive of the drive motor 12a of the table feeding device 12 to rotate the drive shaft 12a in synchronization with the scanning start of each mirror surface 11c of the rotating polygon mirror 11 such that the nut member 12b and the table 12c fixed to the nut member 12b are moved in the sub-scanning direction Y to move the inspection object 3 on the board 3A held on the table 12c in the sub-scanning direction Y. While the linear scanning is performed to the inspection object 3 with the scanning light flux, the control unit 16 stores the photoelectric conversion signal output I of the photodetector 7 in the data storage unit 13 at time intervals when the scanning light fluxes becomes constant interval in the main scanning direction position $x_{di}$ for at least one revolution of the rotating polygon mirror 11 (namely, scanning interval from the point $P1_1$ to the point $P3_6$). The control unit 16 also causes the extraction unit 14a to extract the photoelectric conversion signal output I of the photodetector 7 which is stored in the data storage unit 13, and the control unit 16 causes the appearance positional coordinate computation unit 14b to compute and determine the appearance positional coordinate of the inspection object 3 based on the photoelectric conversion signal output I of the photodetector 7 which is extracted by the extraction unit 12a.

Figure 7A:
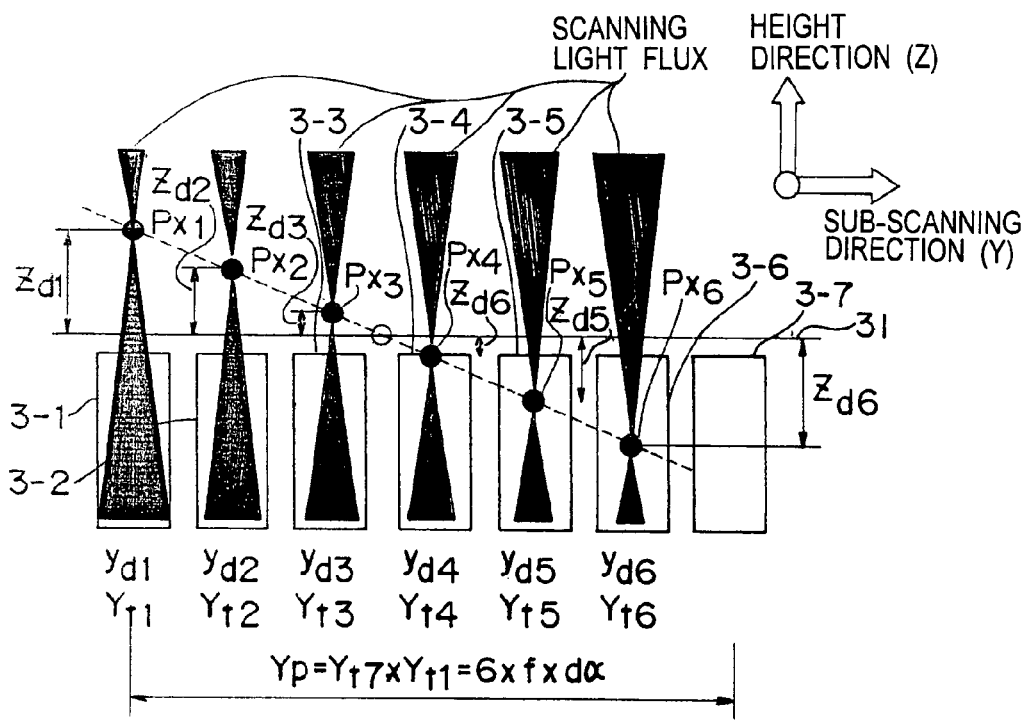
FIG. 7A is a view showing control of a inspection object feeding amount to a sub-scanning direction position, which is performed by a table feeding device of the appearance inspection apparatus and method according to the first embodiment of the present invention.
Figure 7B:
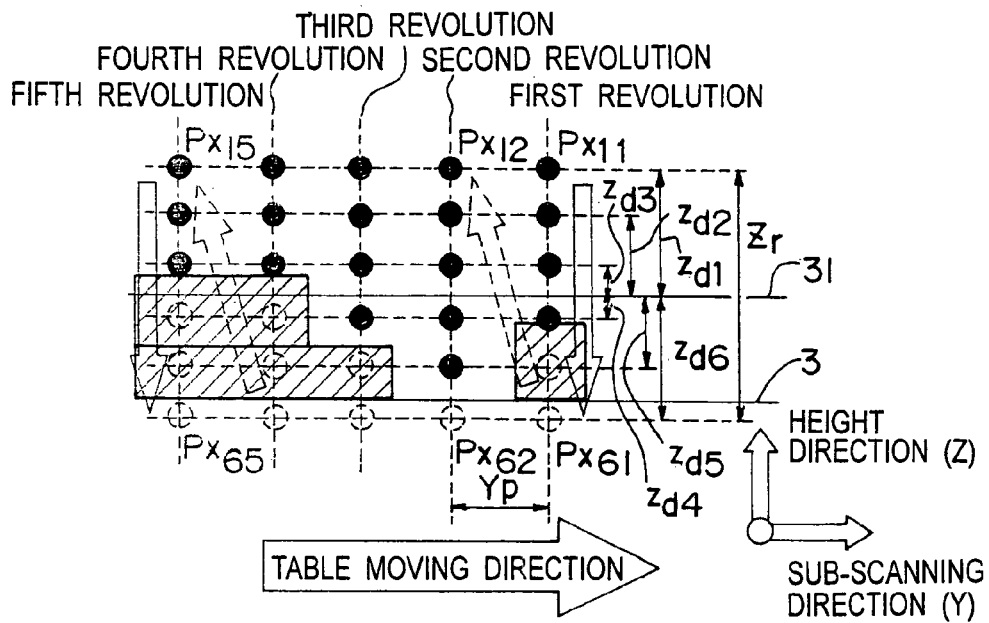
FIG. 7B is a view showing a principle of YZ scanning with respect to the inspection object in the appearance inspection apparatus and method according to the first embodiment of the present invention.

Then, the control of a feeding amount Yt of the inspection object 3 in the sub-scanning direction Y by the table feeding device 12 and a principle of the YZ scanning to the inspection object 3 will be described with reference to FIGS. 7A and 7B. In FIG. 7A, as described above, the sub-scanning direction position $y_{di}$ of the scanning line is changed five times from $y_{d1}$ to $y_{d2}$, . . . , and to $y_{d6}$ during one revolution of the rotating polygon mirror 11 having the six mirror surfaces 11c. At this point, when the feeding amount Yt of table feeding device 12 is changed by the same value as the change amount of sub-scanning direction position $y_{di}$ of the scanning line in synchronization with the scanning operation by each mirror surface 11c of the rotating polygon mirror 11, the scanning line onto the inspection object 3 always scans the same position with respect to the sub-scanning direction position $y_{di}$. That is, in the state in which the table feeding device 12 is stopped, as shown in FIG. 7A, the irradiating light collecting point performs the scanning toward the direction in which the irradiating light collecting point is brought close to the inspection object 3 as the irradiating light collecting point proceeds in the sub-scanning direction Y. On the other hand, when the inspection object 3 is fed in the sub-scanning direction Y by the table feeding device 12, the irradiating light collecting point performs the scanning in the opposite direction (downward direction of FIG. 7B) to the height direction Z as shown in FIG. 7B. As described above, the increase in sub-scanning direction position y is always $f \times d\alpha$ when the mirror surfaces $11c$ of the rotating polygon mirror 11 which deflect the light flux of the light source 1 are changed, so that the inspection object 3 is changed from the position of the inspection object 3-1 to the inspection object 3-6 when the feeding amount Yt is also changed five times from $Yt_1$ to $Yt_6$ at constant increases of $f \times d\alpha$. On the other hand, as described above, the height direction position $z_{di}$ of the irradiating light collecting point of the scanning line is changed five times from $z_{d1}$ to $z_{d2}, \ldots$, and to $z_{d6}$ at constant intervals of $f \times d\alpha \times \tan(\beta)$ During one revolution of the rotating polygon mirror 11, the irradiating light collecting point can be changed in parallel with the height direction Z with respect to the inspection object 3 to perform the Z scanning by controlling the feeding amount Yt of table feeding device 12. The rotating polygon mirror 11 enters the second revolution when the drive motor 12a of the table feeding device 12 and the motor 11a of the rotating polygon mirror 11 are further driven in synchronization with each other. That is, in the rotating polygon mirror 11, the light flux of the light source 1 is sequentially reflected from the first mirror surface $11c_1$ to the sixth mirror surface $11c_6$, and the table feeding device 12 feeds the inspection object 3 in the sub-scanning direction Y at constant feeding intervals of $f \times d\alpha$ while the light flux of the light source 1 is reflected from the first mirror surface $11c_1$ again. Therefore, the inspection object 3 is located at the position of the inspection object 3-7, and the irradiating light collecting point is located at the height direction position $z_{d1}$ in the height direction Z. That is, while the irradiating light collecting point is changed from the height direction position $z_{d1}$ to the height direction position $z_{d6}$ and changed to the height direction position $z_{d1}$ again, the table feeding device 12 moves the inspection object 3 by scanning interval Yp (=Y resolution)=$6 \times f \times d\alpha$ in the sub-scanning direction Y, and the table feeding device 12 moves the inspection object 3 from the position of the inspection object 3-1 to the position of the inspection object 3-7.

FIG. 7B shows the change in irradiating light collecting point of the scanning line with respect to the inspection object 3 by the control operations of the rotating polygon mirror 11 and table feeding device 12. In FIG. 7B, the board on which the plural electronic components (hatched portion of FIG. 7B) are mounted is shown as the inspection object 3. As described above, preferably the inspection range Zr in the height direction Z is set with respect to the inspection object 3 in the range of from the position higher than the uppermost surface of the highest electronic component in the plural electronic components to the position equal to or lower than the board. Accordingly, in FIG. 7B, the point $Px_{11}$, the point $Px_{12}, \ldots$, and the point $Px_{15}$ are set at the positions higher than the electronic component, and the point $Px_{61}$, the point $Px_{62}, \ldots$, and the point $Px_{65}$ are set at the positions lower than the board. In FIG. 7B, a black circle indicates a collecting point of the scanning light flux actually collected by the scanning collective lens 2, and a dotted-line white circle indicates a virtual collecting point in which the scanning light flux is not actually collected because the scanning light flux is reflected from the surface of the inspection object 3 before collected by the scanning collective lens 2.

In the first revolution which is started from the first mirror surface $11c_1$ of the rotating polygon mirror 11, the irradiating light collecting point performs the Z scanning from the point $Px_{11}$ to the point $Px_{61}$ at the same position in the sub-scanning direction Y while the height direction position $z_{di}$ is changed five times from $z_{d1}$ to $z_{d6}$. When the rotating polygon mirror 11 is further rotated to start the scanning of the first mirror surface $11c_1$ again, the sub-scanning direction position $y_{di}$ is changed by Yp to the opposite direction to the sub-scanning direction Y, and the Z scanning is performed while the irradiating light collecting point is changed from $Px_{12}$ to $Px_{62}$. Similarly the sub-scanning direction position $y_{di}$ is changed at constant intervals Yp in each time of one revolution of the rotating polygon mirror 11. The Y scanning is performed to the inspection object 3 at constant intervals Yp in each time of one revolution of the rotating polygon mirror 11. That is, in the appearance inspection apparatus and method of the first embodiment of the present invention, the X scanning can be performed to the inspection object 3 by one mirror surface scanning during the rotating operation of the rotating polygon mirror 11, the Z scanning can be performed by changing the plural mirror surfaces $11c$ having the different mirror surface angles $\lambda$ during one revolution of the rotating polygon mirror 11, and the Y scanning can be performed by rotating the rotating polygon mirror 11 plural times while the inspection object 3 is moved in the sub-scanning direction Y.

At the time the inspection object 3 is irradiated with the light flux, a spot diameter d of the light flux emitted from the light source 1 is changed by the inspection range Zr in the height direction Z of the inspection object 3. Assuming that light intensity of the light flux emitted from the light source 1 has a Gaussian distribution (normal distribution) and $\lambda a$ is a wavelength $\lambda a$, the inspection range Zr and the spot diameter d substantially have a relationship expressed by the following equation.

$$Zr = \pi/4 \div \lambda a \times d^2$$

For example, in the case of the wavelength % a of 600 nm, examples of setting combination of the spot diameter d and the inspection range Zr include (d, Zr)=(30 μm, 1.2 mm), (10 μm, 131 μm), (5 μm, 32.7 μm), and (1 μm, 1.31 μm). For example, in the case where the inspection object 3 is the plural solder pastes applied onto the board, preferably the inspection range Zr in the height direction Z is set in the range of from the position higher than the uppermost surface of the solder paste in the plural solder pastes to the position equal to or lower than the board. In this case, because a thickness of the solder paste is about 0.2 mm at the most, the spot diameter d can be set about 15 μm and the inspection range Zr can be set about 0.3 mm. However, because these setting values are only theoretical values, it is necessary to set the optimum values according to the light flux intensity distribution and the reflection state of the inspection object 3.

Then, a principle of the computation method of determining height information on the inspection object 3 will be described with reference to FIGS. 8A and 8B. The height information on the inspection object 3 is determined from the photoelectric conversion signal output I which is obtained by the incidence of the reflected light to the photodetector 7 through the confocal optical system (reflected light collective lens 5 and shielding plate 6). The reflected light is generated by the X scanning and Z scanning at the same sub-scanning direction position $y_{di}$ of the inspection object 3 during one revolution of the rotating polygon mirror 11.

Figure 8A:
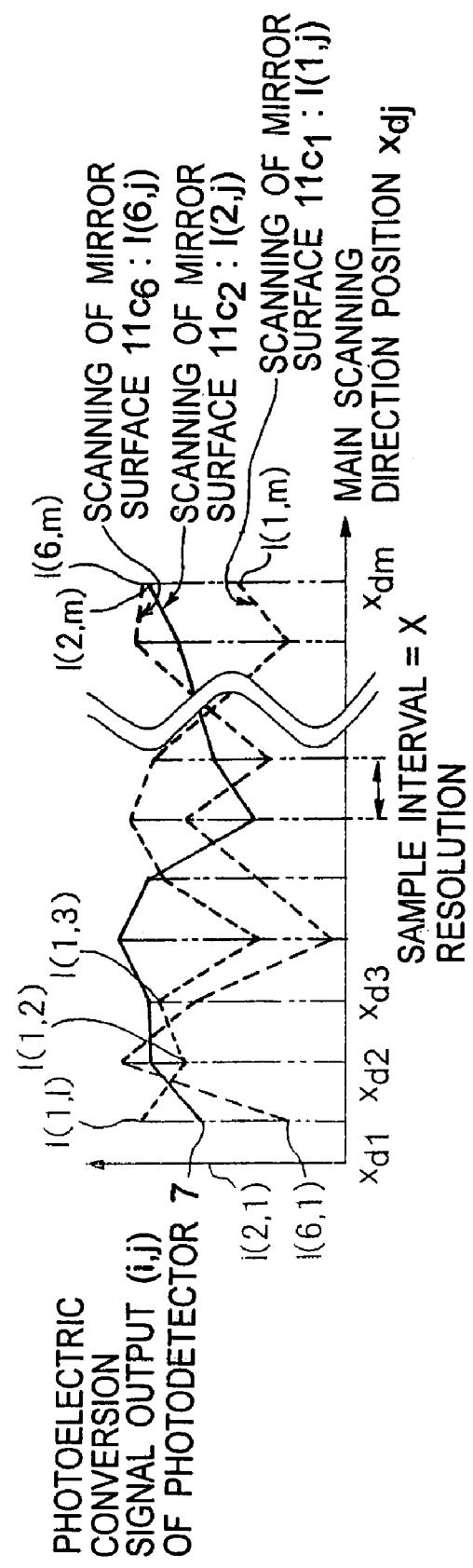
FIG. 8A is a schematic view showing storage contents of a data storage unit of the appearance inspection apparatus and method according to the first embodiment of the present invention.

FIG. 8A schematically shows storage contents of the photoelectric conversion signal output I of the photodetector 7 in the data storage unit 13. The m photoelectric conversion signal outputs I(i, j) of the photodetector 7 are stored in the data storage unit 13 under the control of the control unit 16 at sampling intervals in which the main scanning direction position $x_{dj}$ becomes constant (=X resolution) during the X scanning to the inspection object 3 by one mirror surface $11c$ of the rotating polygon mirror 11. Assuming that j is a sampling number (j=1 to m, and m is integer) in the X direction, the main scanning direction position $x_{dj}$ becomes $x_{d1}, x_{d2}, \ldots$, and $x_{dm}$. The 6×m photoelectric conversion signal outputs I(i, j) of the photodetector 7 are stored in the data storage unit 13 by changing the height direction position $z_{di}$ of the irradiating light collecting point at the same sub-scanning direction position $y_{di}$ five times due to one revolution of the rotating polygon mirror 11 having the six mirror surfaces 11c. In other words, because the mirror surface number i is 1 to 6, when the inspection is performed to the sub-scanning direction positions $y_{d1}$ to $y_{d6}$, the 6×m×6 photoelectric conversion signal outputs I (i, j) of the photodetector 7 are stored in the data storage unit 13.

In FIG. 8A, a polygonal line graph connecting the photoelectric conversion outputs I (1, 1) to I (1, m) of the photodetector 7 with short dotted lines shows the light intensity of the scanning light flux by the first mirror surface $11c_1$. A polygonal line graph connecting the photoelectric conversion outputs I (2, 1) to I (2, m) of the photodetector 7 with long dotted lines shows the light intensity of the scanning light flux at the main scanning direction position $x_{dj}$ by the second mirror surface $11c_2$. A polygonal line graph connecting the photoelectric conversion outputs I (6, 1) to I (6, m) of the photodetector 7 with solid lines shows the light intensity of the scanning light flux at the main scanning direction position $x_{dj}$ by the first mirror surface $11c_6$.

Figure 8B:
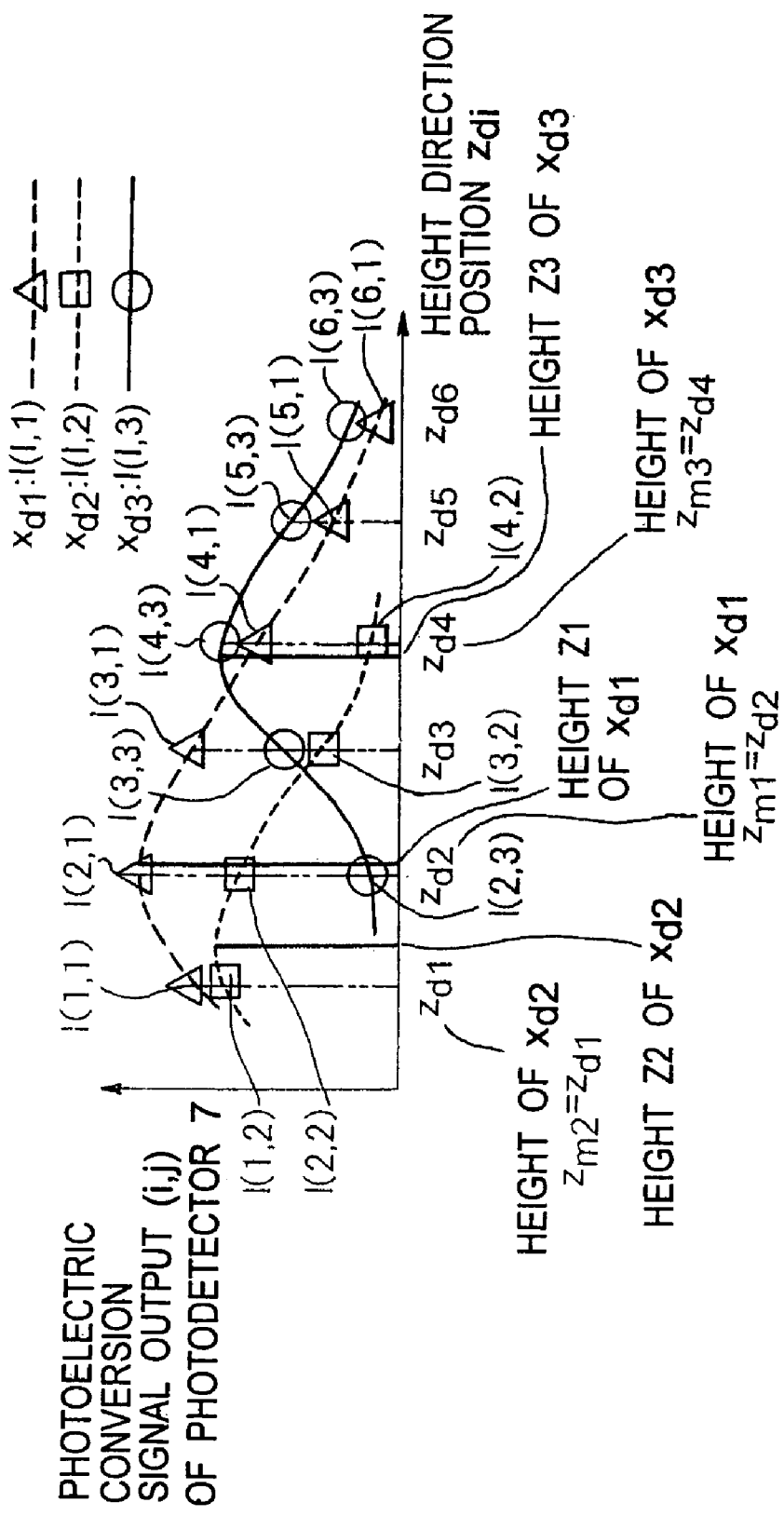
FIG. 8B is a view showing a principle of a computation method performed by an appearance positional coordinate computation unit of the appearance inspection apparatus and method according to the first embodiment of the present invention.

FIG. 8B schematically shows a process method in which the computation unit 14 determines a measured height $z_{mj}$ at each main scanning direction position $x_{dj}$ from the 6×m photoelectric conversion signal outputs I (i, j) corresponding to the one revolution of the rotating polygon mirror 11, which are stored in the data storage unit 13. In the distribution of the six photoelectric conversion signal outputs I (1, 1) to I (6, 1) of the photodetector 7 at the main scanning direction position $x_{d1}$, because the main scanning direction position $x_{dj}$ and sub-scanning direction position $y_{di}$ of the inspection object 3 become the photoelectric conversion signal output I generated at the same point by the Z scanning, as shown by the long dotted line of FIG. 8B, on the basis of the principle of the confocal method, the photoelectric conversion signal output I becomes the maximum curve at the height direction position $z_{d2}$ of the irradiating light collecting point closest to the height Z1 of the inspection object 3 in the main scanning direction position $x_{d1}$. The extraction unit 14a of the computation unit 14 extracts the maximum height direction position $z_{d2}$ as the measured height $z_{m1}$.

In the distribution of the six photoelectric conversion signal outputs I (1, 2) to I (4, 2) of the photodetector 7 at the main scanning direction position $x_{d2}$, because the main scanning direction position $x_{dj}$ and sub-scanning direction position $y_{di}$ of the inspection object 3 become the photoelectric conversion signal output I generated at the same point by the Z scanning, as shown by the short dotted line of FIG. 8B, on the basis of the principle of the confocal method, the photoelectric conversion signal output I becomes the maximum curve at the height direction position $z_{d1}$ of the irradiating light collecting point closest to the height Z2 of the inspection object 3 in the main scanning direction position $x_{d2}$. The extraction unit 14a of the computation unit 14 extracts the maximum height direction position $z_{d1}$ as the measured height $z_{m2}$. In the distribution of the six photoelectric conversion signal outputs I (2, 3) to I (6, 3) of the photodetector 7 at the main scanning direction position $x_{d3}$, because the main scanning direction position $x_{dj}$ and sub-scanning direction position $y_{di}$ of the inspection object 3 become the photoelectric conversion signal output I generated at the same position by the Z scanning, as shown by the solid line of FIG. 8B, on the basis of the principle of the confocal method, the photoelectric conversion signal output I becomes the maximum curve at the height direction position $z_{d4}$ of the irradiating light collecting point closest to the height Z3 of the inspection object 3 in the main scanning direction position $x_{d3}$. The extraction unit 14a of the computation unit 14 extracts the maximum height direction position $z_{d4}$ as the measured height $z_{m3}$. Similarly, the on-scanning line height information on the inspection object 3 can be obtained by extracting each measured height $z_{mj}$ at each main scanning direction position $x_{dj}$.

Figure 8C:
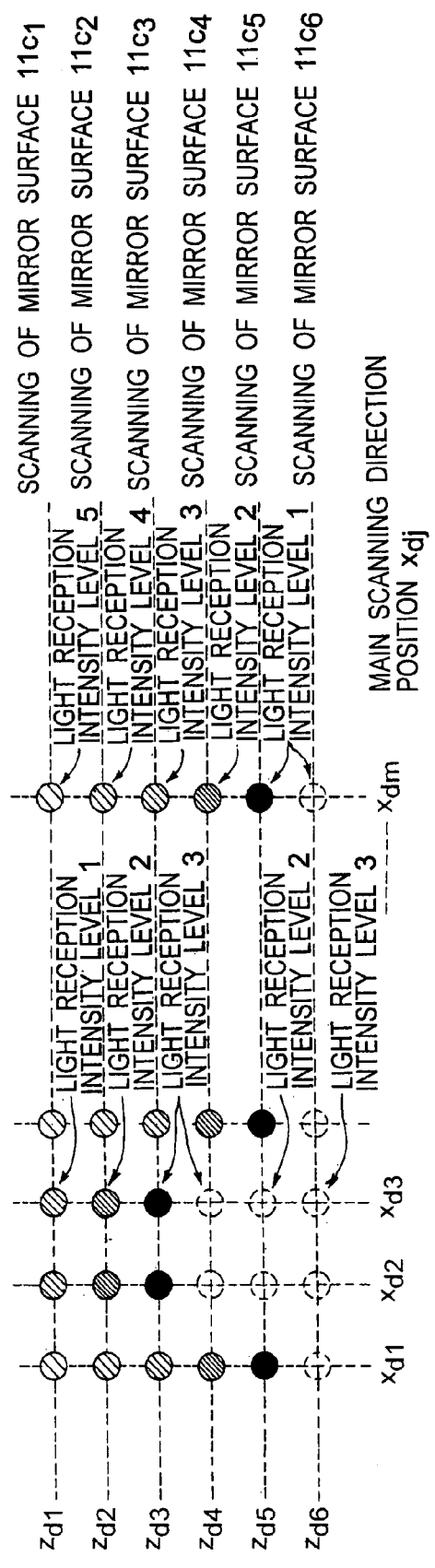
FIG. 8C is a view showing an example of the YZ scanning with respect to the inspection object in the appearance inspection apparatus and method according to the first embodiment of the present invention.

The computation method of determining the height information on the inspection object 3 will be described in detail with reference to FIGS. 2 and 8C to 8E. In this case, as shown in FIG. 2, the description will be made while the electronic component mounted onto the board 3A is assumed to be the inspection object 3. FIG. 8C is a view showing an example of the XZ scanning with respect to the inspection object 3, FIG. 8D is a schematic view showing an example of the storage contents of the data storage unit 13, and FIG. 8E is a view showing an example of the computation method performed by the appearance positional coordinate computation unit 14b.

In FIG. 8C, the black circle indicates a collecting point of the scanning light flux actually collected by the scanning collective lens 2, and the dotted-line white circle indicates a virtual collecting point in which the scanning light flux is not actually collected because the scanning light flux is reflected from the surface of the inspection object 3 before collected by the scanning collective lens 2. In FIG. 8C, the scanning light flux is reflected from the surface of the inspection object 3 before the scanning light flux is collected by the scanning collective lens 2, when the scanning light flux is located at the height direction position $z_{d4}$ and the main scanning direction positions $x_{d2}$ and $x_{d3}$, the height direction position $z_{d2}$ and the main scanning direction positions $x_{d2}$ and $x_{d3}$, and the height direction position $z_{d6}$ and the main scanning direction positions $x_{d1}$ to $x_{dm}$. In FIG. 8C, the X scanning at the height direction position $z_{d1}$ is performed by the first mirror surface $11c_1$ of the rotating polygon mirror 2, the X scanning at the height direction position $z_{d2}$ is performed by the first mirror surface $11c_2$, and similarly the X scannings at the height direction positions $z_{d3}$ to $z_{d6}$ are performed by the second mirror surface $11c_2$ to sixth mirror surface $11c_6$.

The stronger the scanning light flux collected by the scanning collective lens 2 is reflected by the inspection object 3 near the collecting point, the more light intensity of the incident reflected light received by the photodetector 7 is increased. That is, in FIG. 8C, the light intensity of the incident reflected light received by the photodetector 7 becomes strongest in the case of the light reception intensity level 1, the light intensity of the incident reflected light received by the photodetector 7 becomes weaker as the height direction position $z_{di}$ is separated away from the light reception intensity level 1, namely, as the height direction position $z_{di}$ becomes the light reception intensity level 2, the light reception intensity level 3, . . . . Accordingly, for example, in the main scanning direction position $x_{d3}$, the scanning light flux is collected with the light reception intensity level 3 at the height direction position $z_{d1}$, the scanning light flux is collected with the light reception intensity level 2 at the height direction position $z_{d2}$, the scanning light flux is collected with the light reception intensity level 1 at the height direction position $z_{d3}$, and the collecting point of the scanning light flux is formed. On the other hand, the scanning light flux should be collected with the light reception intensity level 1 at the height direction position $z_{d4}$, the scanning light flux should be collected with the light reception intensity level 2 at the height direction position $z_{d5}$, and the scanning light flux should be collected with the light reception intensity level 3 at the height direction position $z_{d6}$. However, the scanning light fluxes have the virtual collecting points because the scanning light fluxes are actually reflected from the surface of the inspection object 3.

Figure 8D:
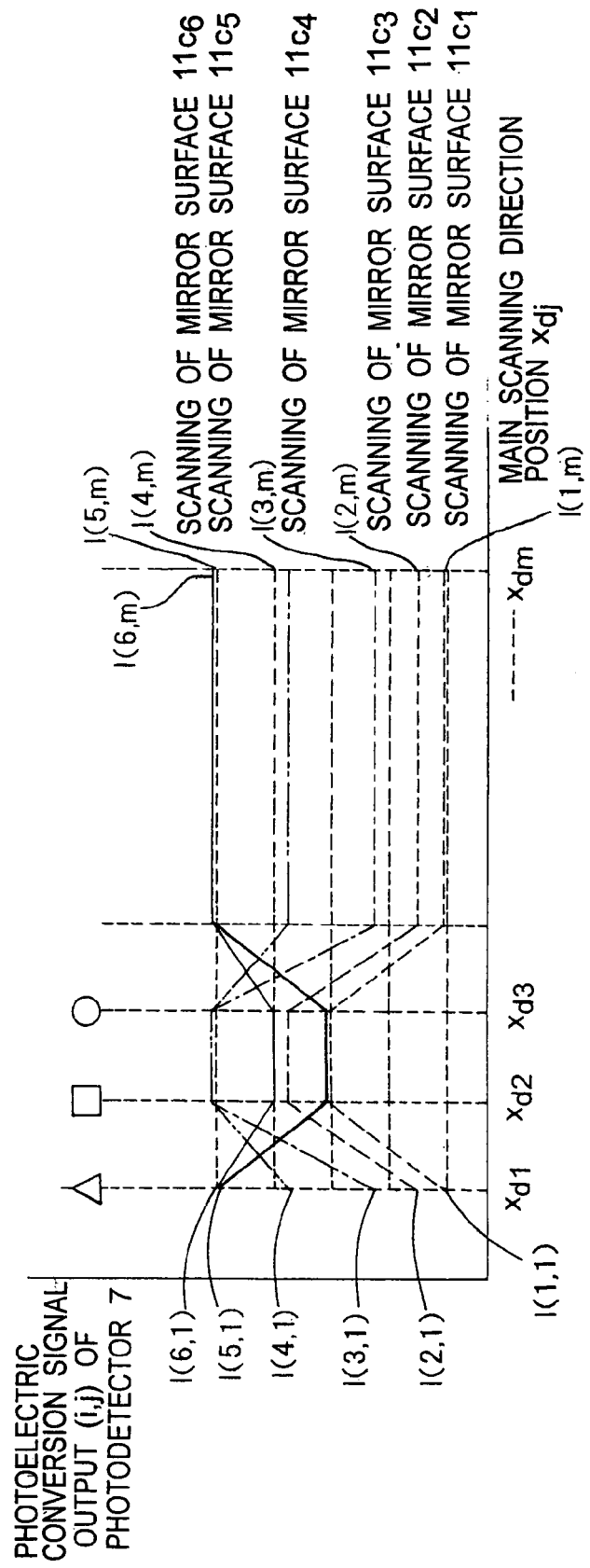
FIG. 8D is a schematic view showing an example of the storage contents of the data storage unit of the appearance inspection apparatus and method according to the first embodiment of the present invention.
Figure 8E:
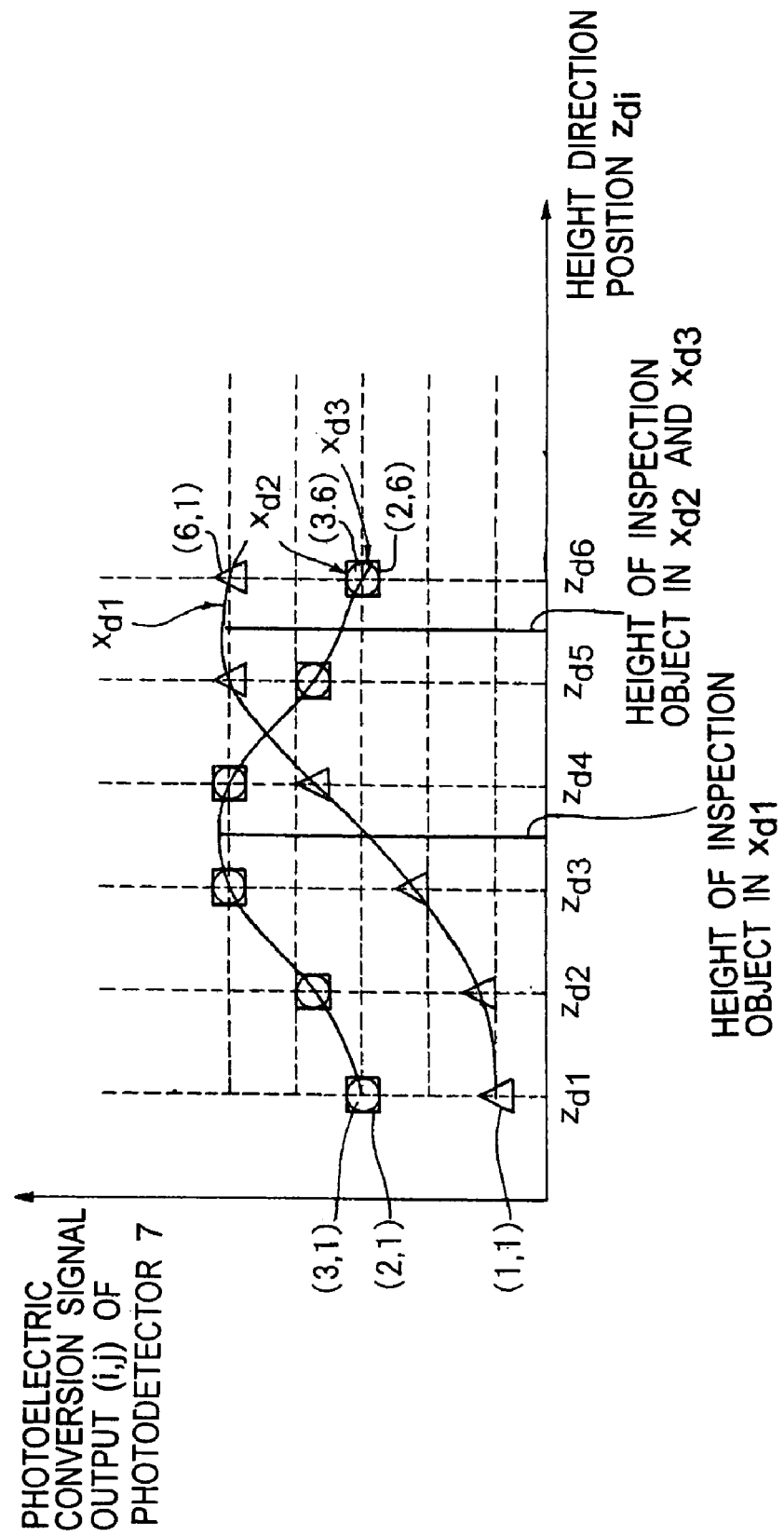
FIG. 8E is a view showing an example of the computation method performed by the appearance positional coordinate computation unit of the appearance inspection apparatus and method according to the first embodiment of the present invention.

FIG. 8D is a graph showing a relationship between the main scanning direction position $x_{dj}$ and the photoelectric conversion signal output I obtained by performing the photoelectric conversion to the light reception intensity levels 1 to 5 shown in FIG. 8C with the photodetector 7. In FIG. 8D, the long dotted lines connecting the photoelectric conversion outputs I (1, 1) to I (1, m) of the photodetector 7 show the light intensity of the scanning light flux at the main scanning direction position $x_{dj}$ by the first mirror surface $11c_1$. The short dotted lines connecting the photoelectric conversion outputs I (2, 1) to I (2, m) of the photodetector 7 show the light intensity of the scanning light flux at the main scanning direction position $x_{dj}$ by the second mirror surface $11c_2$. The alternate long and short dash lines connecting the photoelectric conversion outputs I (3, 1) to I (3, m) of the photodetector 7 show the light intensity of the scanning light flux at the main scanning direction position $x_{dj}$ by the third mirror surface $11c_3$. The alternate long and two short dash lines connecting the photoelectric conversion outputs I (4, 1) to I (4, m) of the photodetector 7 show the light intensity of the scanning light flux at the main scanning direction position $x_{dj}$ by the fourth mirror surface $11c_4$. The straight lines connecting the photoelectric conversion outputs I (5, 1) to I (5, m) of the photodetector 7 show the light intensity of the scanning light flux at the main scanning direction position $x_{dj}$ by the fifth mirror surface $11c_5$. The bold straight lines connecting the photoelectric conversion outputs I (6, 1) to I (6, m) of the photodetector 7 show the light intensity of the scanning light flux at the main scanning direction position $x_{dj}$ by the sixth mirror surface $11c_6$.

FIG. 8E is a graph, in which the photoelectric conversion signal output I of each height direction position $z_{di}$ is marked at each main scanning direction position $x_{dj}$ and the marks are connected with a smooth curve. In FIG. 8E, triangle marks indicate the photoelectric conversion signal outputs I (1, 1) to I (6, 1) of each height direction position $z_{di}$ (scannings from the first mirror surface $11c_1$ to the sixth mirror surface $11c_6$) at the main scanning direction position $x_{d1}$. Similarly, in FIG. 8E, square marks indicate the photoelectric conversion signal outputs I (2, 1) to I (2, 6) of each height direction position $z_{di}$ at the main scanning direction position $x_{d2}$, and circular marks indicate the photoelectric conversion signal outputs I (3, 1) to I (3, 6) of each height direction position $z_{di}$ at the main scanning direction position $x_{d3}$.

As shown in FIG. 8E, in the case of the main scanning direction position $x_{d1}$ (triangle), the photoelectric conversion signal output I becomes the maximum between the height direction position $z_{d5}$ and the height direction position $z_{d6}$. The extraction unit 14a of the computation unit 14 extracts the height between the height direction position $z_{d5}$ and the height direction position $z_{d6}$ as the measured height $z_{m1}$ at the main scanning direction position $x_{d1}$ of the inspection object 3. In the case of the main scanning direction position $x_{d2}$ (square) or the main scanning direction position $x_{d3}$ (circle), the photoelectric conversion signal output I becomes the maximum between the height direction position $z_{d3}$ and the height direction position $z_{d4}$. The extraction unit 14a of the computation unit 14 extracts the height between the height direction position $z_{d3}$ and the height direction position $z_{d4}$ as the measured height $z_{m2}$ or $z_{m13}$ at the main scanning direction position $x_{d2}$ or $x_{d3}$ of the inspection object 3. Similarly, the on-scanning line height information on the inspection object 3 can be obtained by extracting each measured height $z_{mj}$ at each main scanning direction position $x_{dj}$ with the extraction unit 14a.

As described above, because the height direction position $z_{di}$ is discretely changed at intervals of $f \times d\alpha \times \tan(\beta)$, when the extraction unit 14a extracts the height direction position $z_{di}$ which becomes the maximum, the interval of the measured height $z_{mi}$ also becomes discrete value of $f \times d\alpha \times \tan(\beta)$ (namely, measured height resolution becomes $f \times d\alpha \times \tan(\beta)$). However, when the appearance positional coordinate computation unit 14a performs a computation process such as multinomial interpolation, the midpoint between the adjacent height direction positions $z_{di}$ can be determined as the measured height $z_{mi}$ to improve the height resolution.

In order to perform the computation process such as the multinomial interpolation, it is necessary to correlate the photoelectric conversion signal output I of the photodetector 7 stored in the data storage unit 13 and the mirror surface number i of the rotating polygon mirror 11. Therefore the control unit 16 causes to the appearance positional coordinate computation unit 14b to output a signal (hereinafter referred to as rotation synchronous signal) which is synchronous with the rotation of the rotating polygon mirror 11 in each one revolution. The control unit 16 also caused the appearance positional coordinate computation unit 14b to output a signal (hereinafter referred to as scanning synchronous signal) which is synchronous with the scanning operation of each mirror surface 11c in each mirror surface scanning. The appearance positional coordinate computation unit 14b can correlate the photoelectric conversion signal output I of the photodetector 7 and the mirror surface number i of the rotating polygon mirror 11 by the combination of the rotation synchronous signal and the scanning synchronous signal.

Thus, according to the appearance inspection apparatus and method of the first embodiment of the present invention, the data of the photoelectric conversion signal output I of the photodetector 7 in one revolution of the rotating polygon mirror 11 is stored in the data storage unit 13, and the computation unit 14 determines the height direction position $z_{di}$ in which the photoelectric conversion signal output I becomes the maximum at the same point of the main scanning direction position $x_{dj}$ and the sub-scanning direction position $y_{di}$ among the data stored in the data storage unit 13. Therefore, the height information (namely, XZ cross section shape) concerning the inspection object 3 can be obtained on the scanning line. According to the appearance inspection apparatus and method of the first embodiment of the present invention, as shown in FIG. 7B, the control unit 16 performs the control such that the feeding amount Yt of table feeding device 12 is synchronized with the constant-angular-speed rotation of the rotating polygon mirror 11 to locate the plural irradiating light collecting point by each mirror surface at the height directions Z of the inspection object 3. Therefore, the information on the height direction position $z_{mi}$ (i.e., positional coordinate) can be obtained at each main scanning direction position $x_{dj}$ and each sub-scanning direction position $y_{di}$ in the XY scanning range of the inspection object 3. According to the appearance inspection apparatus and method of the first embodiment of the present invention, for example, in FIGS. 7B and 8A, the computation unit 14 determines the appearance positional coordinates of the inspection object 3, i.e., the total points (m×5×6=) 30×m of the m points (the number of samplings in the main scanning direction X) in the main scanning direction, the five points (the number of revolutions of the rotating polygon mirror 11) in the sub-scanning direction, and the six points (the number of mirror surfaces of the rotating polygon mirror) in the height direction. Therefore, the appearance of the inspection object can be inspected in a stereoscopic manner.

As described above, the method of moving the inspection object 3 in the sub-scanning direction Y with the table feeding device 12 is described in the first embodiment. Alternatively, the same effect can be obtained by a method in which the inspection object 3 is fixed while the whole optical system is moved in the sub-scanning direction Y. Although the f-θ lens is used as the scanning collective lens 2 in the first embodiment, the same effect can be obtained even if the linearly proportional relationship does not hold between the main scanning direction position $x_{dj}$ and the incident angle θ (for example, $x_d = f \times \sin(\theta)$ or $x_d = f \times \tan(\theta)$).

SECOND EMBODIMENT

Figure 9A:
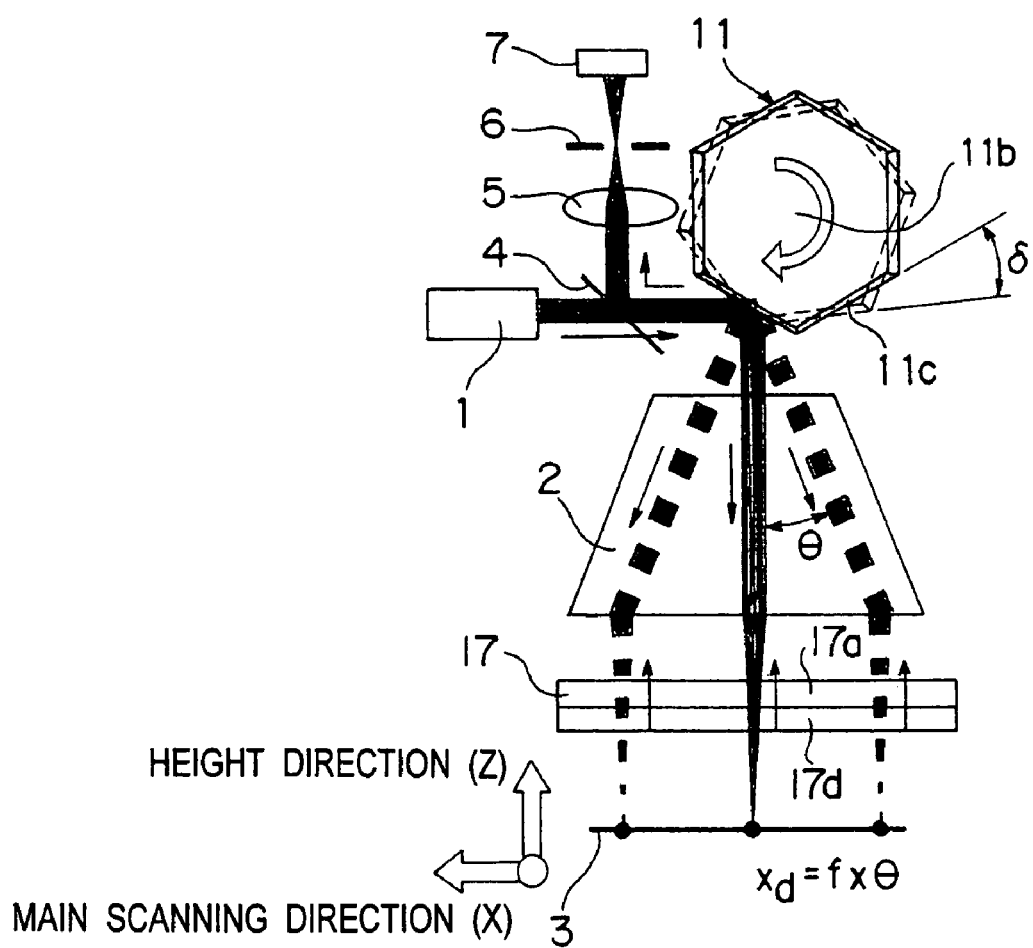
FIG. 9A is a schematic view showing a configuration of an optical system of an appearance inspection apparatus and method according to a second embodiment of the present invention when viewed from the sub-scanning direction.
Figure 9B:
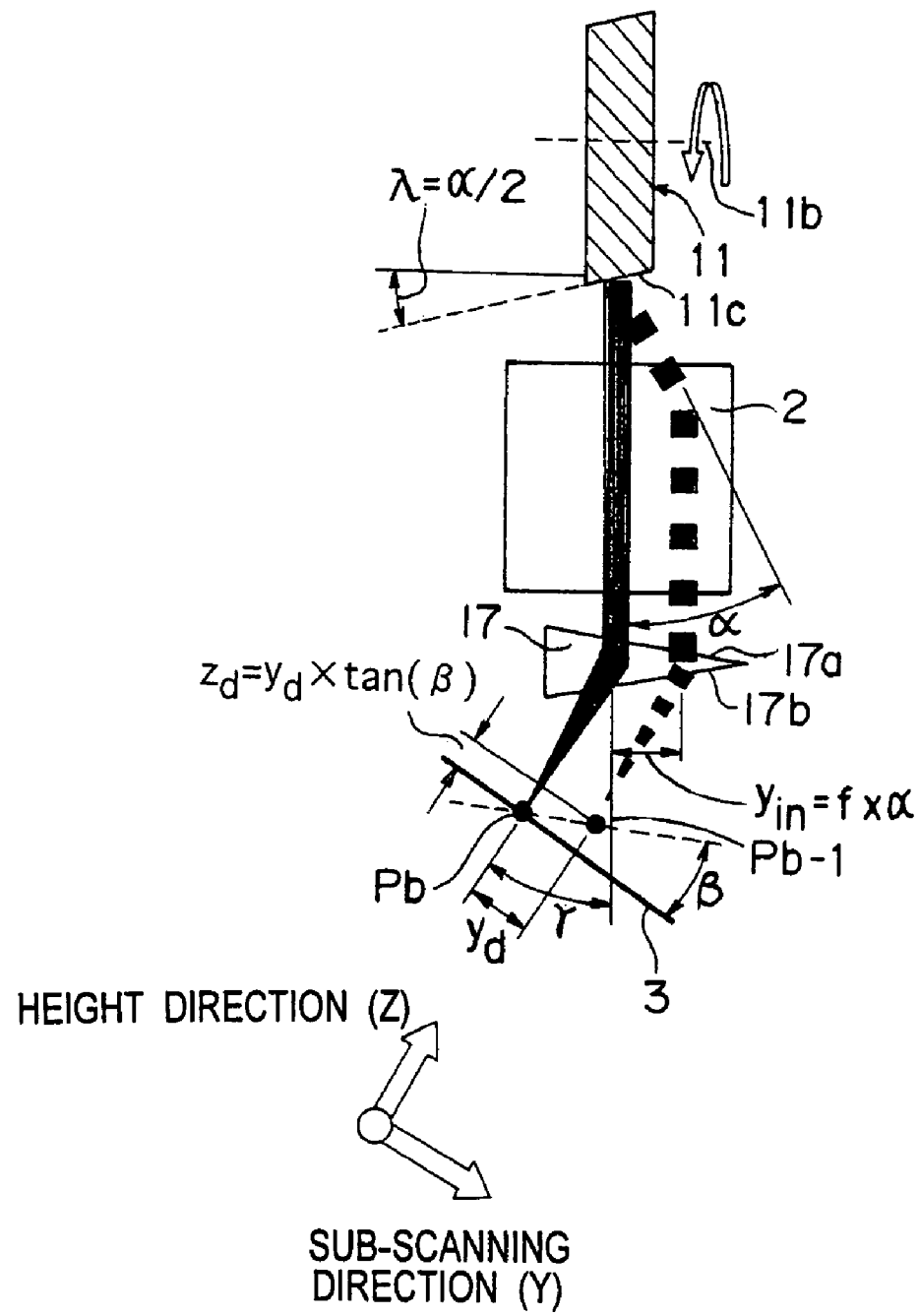
FIG. 9B is a schematic view showing the configuration of the optical system of the appearance inspection apparatus and method according to the second embodiment of the present invention when viewed from a main-scanning direction.

FIG. 9A is a schematic view showing a configuration of an optical system of an appearance inspection apparatus and method according to a second embodiment of the present invention when viewed from the sub-scanning direction Y. FIG. 9B is a schematic view showing the configuration of the optical system of the appearance inspection apparatus and method according to the second embodiment of the present invention when viewed from a main-scanning direction X.

As shown in FIGS. 9A and 9B, the appearance inspection apparatus and method of the second embodiment of the present invention differs from the appearance inspection apparatus of the first embodiment in that the appearance inspection apparatus and method of the second embodiment includes a scanning collective lens 2A and a wedge-shape long prism 15. The scanning collective lens 2A is arranged in parallel with the height direction Z while the optical axis of the scanning collective lens 2 is not inclined by the angle β from the plane orthogonal to the rotation axis 11b of the rotating polygon mirror 11. The long prism 15 constitutes an example of the collecting point position forming optical system between the scanning collective lens 2A and the inspection object 3, and the long prism 15 has an incident plane and an outgoing plane which are parallel to the main scanning direction X. Other components and configurations of the appearance inspection apparatus of the second embodiment are similar to that of the first embodiment, so that the overlapping description will be omitted.

As shown in FIGS. 9A and 9B, because the incident plane 17a and outgoing plane 17b of the long prism 17 are arranged in parallel with the main scanning direction X, the scanning light flux passes through the long prism 17, the scanning light flux is not folded in the plane perpendicular to the sub-scanning direction Y, but the scanning light flux is folded by an angle γ only in the plane perpendicular to the main scanning direction X by the refraction action, and then the scanning light flux is collected at a irradiating light collecting point Pb. The rotation of the rotating polygon mirror 11 performs the linear scanning onto the inspection object 3 in the main scanning direction X with the scanning light flux collected at the collecting point Pb. In the case where the mirror surface angle of the rotating polygon mirror 11 is λ=α/2, as with the first embodiment, the scanning light flux outputted from the scanning collective lens 2 is incident to the long prism 17 while moved by a distance $y_{in} = f \times \alpha$ in parallel to the sub-scanning direction Y. In the scanning light flux incident to the long prism 17, a parallel moving amount is changed from the distance $y_{in}$ to a distance $y_d$ by the action of the long prism 17, the position of the irradiating light collecting point Pb-1 is shifted by the distance $y_d$ in the sub-scanning direction Y and by a distance $z_d$ in the height direction Z with respect to the irradiating light collecting point Pb where the scanning light flux passes through the optical axis center of the scanning collective lens 2.

The second embodiment differs from the first embodiment in that the long prism 17 is newly provided and the inclination β of the scanning collective lens 2 is eliminated. However, in both the first embodiment and the second embodiment, the X scanning and the YZ scanning can simultaneously be performed to the inspection object 3 by the mirror surface angle λ of the rotating polygon mirror 11, and the same effect can be exerted.

Figure 10A:
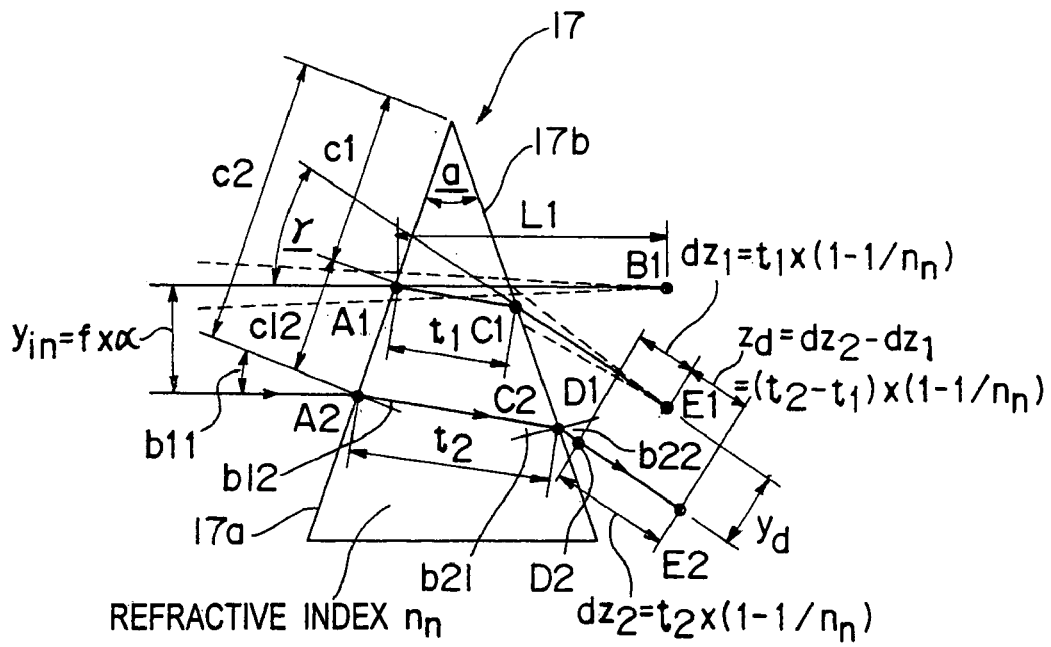
FIG. 10A is a view explaining long prism action of the appearance inspection apparatus and method according to the second embodiment of the present invention.
Figure 10B:
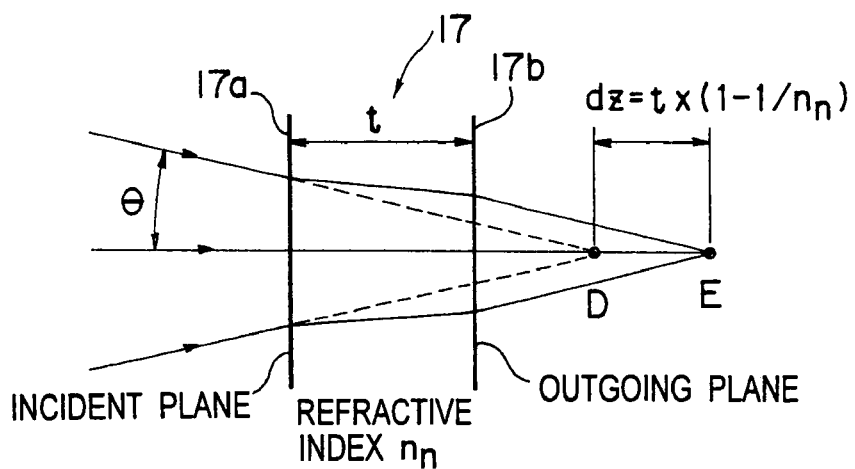
FIG. 10B is a view explaining movement of an irradiating light collecting point performed by the long prism in the appearance inspection apparatus and method according to the second embodiment of the present invention.
Figure 11A:
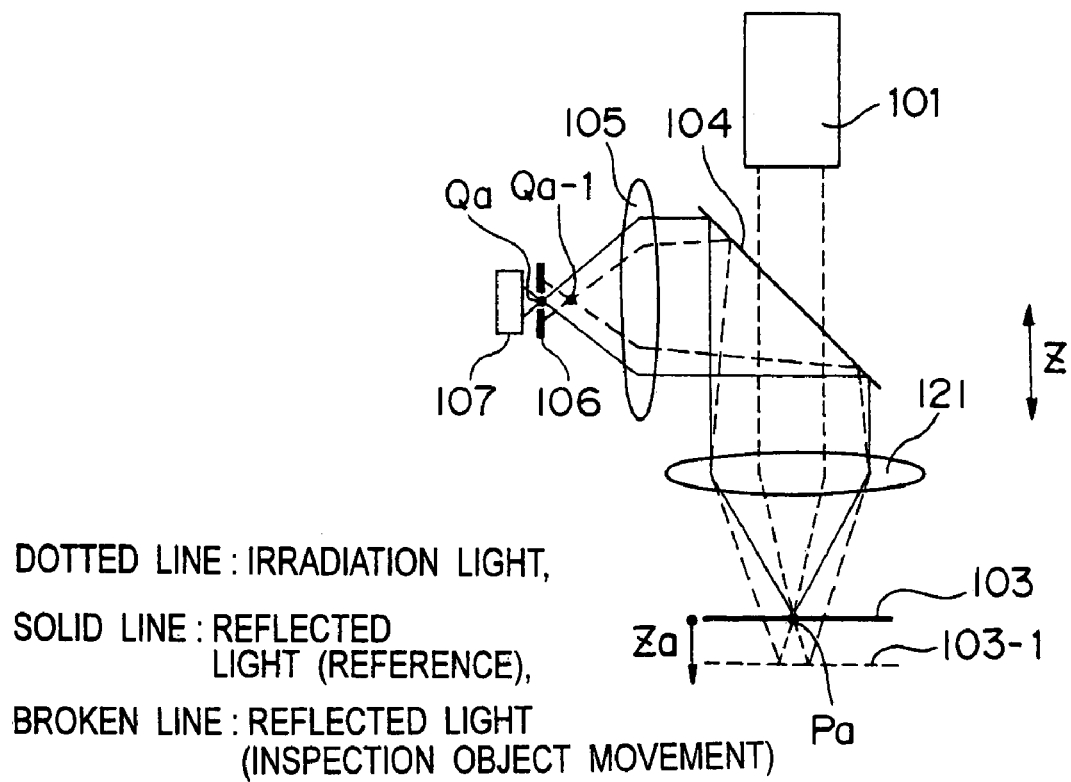
FIG. 11A is a view showing a configuration of the optical system of a conventional confocal type appearance inspection apparatus.
Figure 11B:
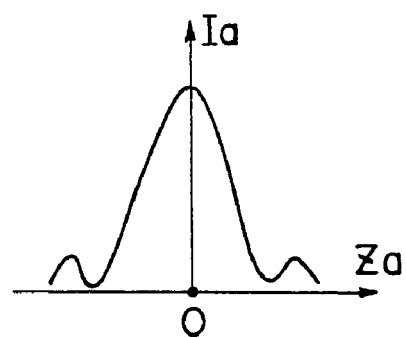
FIG. 11B is a view showing a positional relationship between a photoelectric conversion signal output of a photodetector and the inspection object in the conventional confocal type appearance inspection apparatus.
Figure 12A:
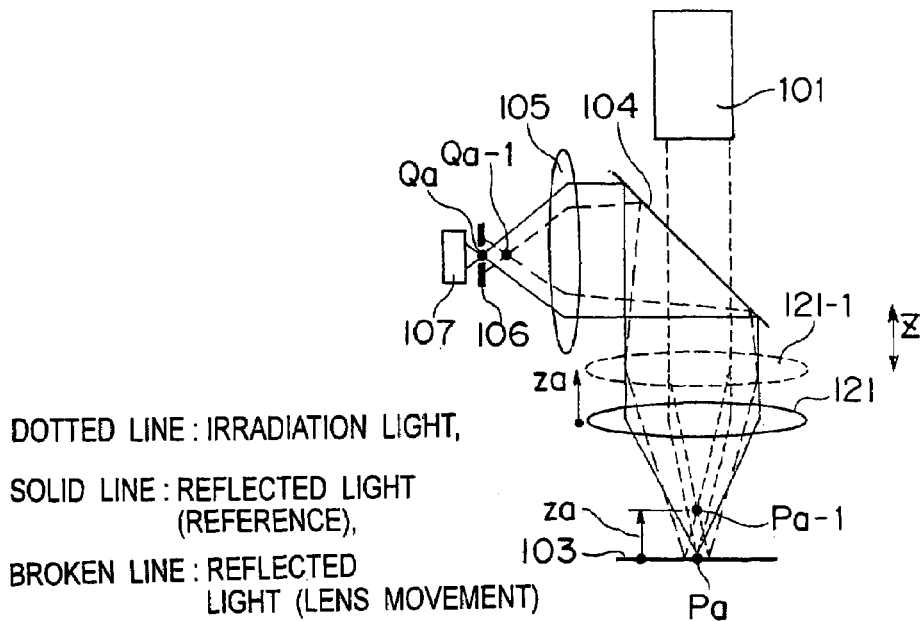
FIG. 12A is a view showing an example 1 (movement of collective lens) of Z scanning in the conventional confocal type appearance inspection apparatus.
Figure 12B:
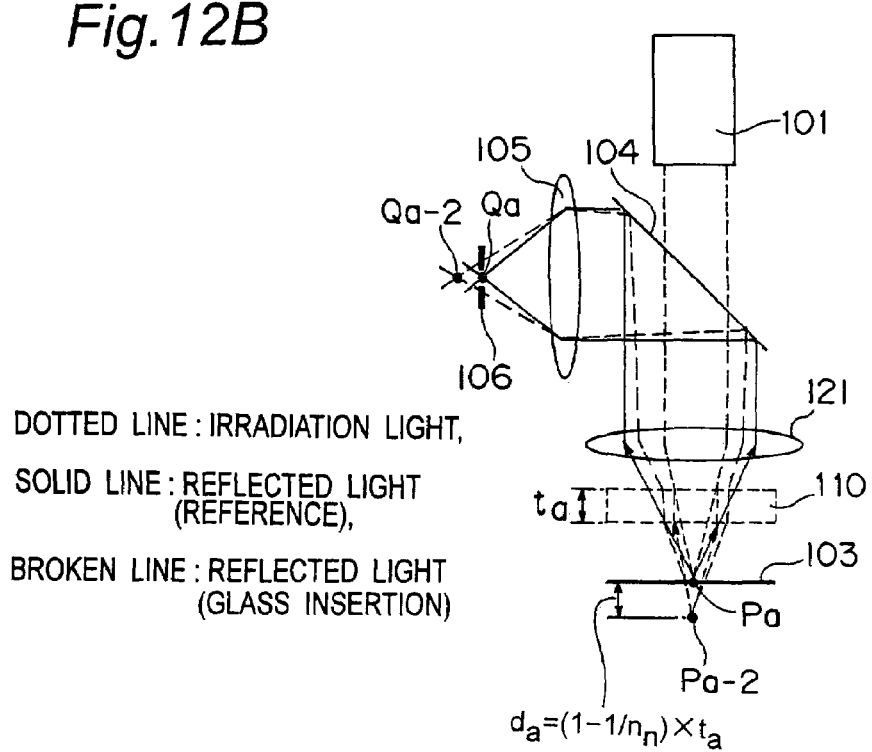
FIG. 12B is a view showing an example 2 (insertion of parallel glass) of the Z scanning in the conventional confocal type appearance inspection apparatus.

The action of the long prism 17 will be described in detail with reference to FIGS. 10A and 10B. FIG. 10A is a view explaining the action of the long prism 17, and FIG. 10B is a view explaining the movement of the irradiating light collecting point performed by the long prism 17. As shown in FIG. 10A, assuming that a is a vertical angle of the long prism 17 and $n_n$ is a refractive index, when the light flux of the light source 1 is incident from a point A2 on the incident plane 17a of the long prism 17 while outputted from a point C2 on the outgoing plane 17b, an angle (hereinafter referred to as folded angle) γ in which the scanning light flux outputted from the scanning collective lens 2 is folded by the long prism 17 is expressed by the following equations according to a Snell's law and a geometrical relationship. At this point, it is assumed that b11 is an angle (hereinafter referred to as incident angle) formed by the incident plane 17a and the scanning light flux (hereinafter referred to as incident light) which is outputted from the scanning collective lens 2 and incident to the long prism 17. It is also assumed that b12 is an angle formed by the incident plane 17a and the scanning light flux incident to the inside of the long prism 17 and b21 is an angle formed by the outgoing plane 17b and the scanning light flux incident to the inside of the long prism 17. It is also assumed that b22 is an angle formed by the outgoing plane 17b and the scanning light flux (hereinafter referred to as outgoing light) outputted from the long prism 17.

$\sin(b12) = \sin(b11)/n_n$ (Snell's law at the point A2)

$\sin(b22) = \sin(b21) \times n_n$ (Snell's law at the point C2)

$a = b21 + b12$ (geometrical relationship of the triangle)

$\gamma = (b11 - b12) - (b21 - b22)$ (geometrical relationship)
$= b11 + b22 - a = f1(a, n_n, b11)$ That is, the folded angle γ becomes a function f1 (a, $n_n$, b11) of the vertical angle a, the refractive index $n_n$, and the incident angle b11. Accordingly, the scanning light flux passing through the points A1 to C1 moved by the distance $y_{in}$ in parallel with the sub-scanning direction Y has the same incident angle b11 as the scanning light flux passing through the points A2 to C2, so that the folded angle becomes γ in the scanning light flux passing through the points A1 to C1. That is, the outgoing light which passes through the points A1 to C1 and is outputted from the point C1 becomes parallel to the outgoing light which passes through the points A2 to C2 and is outputted from the point C2.

The distance $y_d$ between the outgoing light outputted from the point C1 and the outgoing light outputted from the point C2 has a linearly proportional relationship with the distance Yin between the incident light incident to the point A1 and the incident light incident to the point A2, and a coefficient of the linearly proportional relationship is obtained from the Snell's law as follows. Consequently, the proportional coefficient becomes a function f2(a, $n_n$, b11) of the vertical angle a, the refractive index $n_n$, and the incident angle b11.

$$y_d/y_{in} = \cos(b12)/\cos(b11) \times \cos(b22)/\cos(b21) = f2(a, n_n, b11)$$

As shown in FIG. 9B, the irradiating light collecting point Pb is moved to the irradiating light collecting point Pb–1 by the distance $y_d$ in the proceeding direction of the scanning light flux due to the action.

The movement in the height direction Z of the irradiating light collecting point Pb by the long prism 17 will be described below. As shown in FIG. 10B, when the scanning light flux having the small collecting angle θ is incident to the long prism 17 having the thickness t and refractive index $n_n$, the irradiating light collecting point is moved by $dz = t \times (1 - 1/n_n)$ in the scanning light flux proceeding direction from the point D to the point E by the Snell's law and paraxial approximation ($\sin(\theta) \approx \theta$) In FIG. 10A, in the case where the incident light is collected at the point B1 which is located at a distance L1 away from the point A1 unless the incident light incident to the point A1 passes through the long prism 17, an irradiating light collecting point E1 of the outgoing light which passes through the point A1 to the point C1 and is outputted from the point C1 is moved by the distance $dz_1 = t_1 \times (1 - 1/n_n)$ in the scanning light flux proceeding direction ($t_1$ = distance A1C1) with respect to a point D1 (distance A1B1 = distance A1C1 + distance C1D1 = L1) which is located at the distance L1 away from the point A1 along the path of the scanning light flux folded by the long prism 17.

Similarly the irradiating light collecting point of the incident light incident to the point A2 becomes a point E2 which is moved by the distance $dz_2 = t_2 \times (1 - 1/n_n)$. That is, even in the scanning light fluxes which have the same distance to the irradiating light collecting point unless passing through the long prism 17, the positions of the irradiating light collecting points differ from each other by the $z_d = (t_2 - t_1) \times (1 - 1/n_n)$ in the scanning light flux proceeding direction, when the incident points differs from each other (for example, points A1 and A2) to the incident plane 17a of the long prism 17. At this point, as is clear from the geometrical relationship of the triangle, a difference ($t_2 - t_1$) in distance passing through the long prism 17 is linearly proportional to a distance c12 between the points A1 and A2, and the proportional coefficient becomes a function of the vertical angle a and the incident angle b12. Because of the relationship of $c12 = y_{in}/\cos(b11)$, eventually $z_d$ is linearly proportional to the distance Yin, and the proportional coefficient becomes a function f3 of the vertical angle a, the refractive index $n_n$, and the incident angle b11.

$$z_d/y_{in} = f3(a, n_n, b11)$$

Accordingly, as shown in FIG. 9B, the scanning light flux is folded by the angle γ due to the action of the long prism 17, the scanning light flux is moved from the point pb of the irradiating light collecting point to the point Pb–1' (by the distance $y_d$ in the sub-scanning direction Y and by the distance $z_d$ in the height direction Z), and the straight line connecting the point Pb and the point Pb–1 is inclined by the angle β of the following equation with respect to the plane perpendicular to the scanning light flux proceeding direction.

$$\tan(\beta) = z_d/y_d = f3(a, n_n, b11)/f2(a, n_n, b11)$$

That is, the height direction position $z_{di}$ and the sub-scanning direction position $y_{di}$ can be changed with respect to the inspection object 3 to increase a degree of freedom in design by changing the three parameters (vertical angle a, refractive index $n_n$, and incident angle b11) of the long prism 17.

It is to be noted that, by properly combining the arbitrary embodiments of the aforementioned various embodiments, the effects possessed by them can be produced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The disclosure of Japanese Patent Application No. 2005-116869 filed on Apr. 14, 2005 including specification, drawing and claims are incorporated herein by reference in its entirety.

INDUSTRIAL APPLICABILITY

The appearance inspection apparatus and method according to the present invention has the effect of accurately determining the appearance coordinate of the inspection object at high speed by adding the simple function to the linear scanning optical system of the rotating polygon mirror. Particularly, the present invention is useful to the appearance inspection apparatus for the object spreading on the plane. Specifically, the present invention is useful to the appearance inspection apparatus and method for inspecting the electronic component mounted state or the solder paste applied state in a process of soldering the mounting board.

The invention claimed is:

1. An appearance inspection apparatus comprising:
    a light source for emitting a light flux;
    a rotating polygon mirror which has at least three mirror surfaces in an outer peripheral portion thereof, is arranged to be rotatable about a rotation axis thereof at a constant angular speed, for deflecting the light flux emitted from the light source toward an inspection object by each of the mirror surfaces, so as to linearly scan the light flux in a main scanning direction by a rotation;
    a collecting point position forming optical system for moving a collecting point in an inspection range in a height direction orthogonal to the main scanning direction of the inspection object while the light flux, deflected and scanned by each of the mirror surfaces of the rotating polygon mirror, is collected at the collecting point by the rotation of the rotating polygon mirror;
    a photodetector for performing photoelectric conversion of light intensity of reflected light, which is reflected by the inspection object after passing through the collecting point position forming optical system and is deflected by the mirror surface of the rotating polygon mirror through the collecting point position forming optical system, into a photoelectric conversion signal output, the light intensity depending on a distance between the collecting point and a reflection point of the light flux on the inspection object;
    an inspection object moving device for moving the inspection object in a sub-scanning direction orthogonal to both the main scanning direction and the height direction in synchronization with the rotation of the rotating polygon mirror at the constant angular speed; and
    a computation unit for determining an appearance positional coordinate of the inspection object to perform appearance inspection of the inspection object based on the photoelectric conversion signal output of the reflected light to which the photoelectric conversion is performed by the photodetector, wherein the rotating polygon mirror is configured such that mirror surface angles which are of angles formed between the mirror surfaces and the rotation axis of the rotating polygon mirror differ from one another in the mirror surfaces in order to shift the collecting point of the light flux in the sub-scanning direction in association with the rotation at the constant angular speed, and the inspection object moving device moves the inspection object in the sub-scanning direction in order to linearly scan the collecting point in the height direction of the inspection object during one revolution of the rotating polygon mirror at the constant angular speed, the collecting point being shifted in the sub-scanning direction by each of the mirror surfaces while moved in the inspection range in the height direction by the collecting point position forming optical system and, before the further one revolution at the constant angular speed is started by the rotating polygon mirror, the inspection object moving device moves the inspection object in the sub-scanning direction to perform the appearance inspection at a portion, different from a portion to which the appearance inspection is already performed during the one revolution of the rotating polygon mirror, on the inspection object by the linear scanning of the collecting point in the main scanning direction and the movement of the collecting point in the height direction in the inspection range.

2. The appearance inspection apparatus according to claim 1, wherein the collecting point position forming optical system includes a scanning collective lens which is arranged such that an optical axis thereof is inclined with respect to a direction orthogonal to the rotation axis of the rotating polygon mirror, for collecting the light flux deflected and scanned by each of the mirror surfaces of the rotating polygon mirror, at the collecting point which is moved in the inspection range in the height direction while linearly moved in the main scanning direction.

3. The appearance inspection apparatus according to claim 1, wherein the collecting point position forming optical system includes:

a scanning collective lens which is arranged such that an optical axis thereof is parallel to a direction orthogonal to the rotation axis of the rotating polygon mirror, for collecting the light flux deflected and scanned by each of the mirror surfaces of the rotating polygon mirror, at the collecting point; and a prism which is arranged between the scanning collective lens and the inspection object such that an incident plane thereof and an outgoing plane thereof are parallel to the main scanning direction, for deflecting the light flux incident from the incident plane and outputting the light flux from the outgoing plane, and the light flux passing through the scanning collective lens is incident from the incident plane of the prism, the light flux is deflected to be outputted from the outgoing plane, thereby the collecting point is moved in the inspection range in the height direction while linearly moved in the main scanning direction.

4. The appearance inspection apparatus according to claim 1, further comprising a data storage unit in which the photoelectric conversion signal output of the reflected light is stored, the reflected light being outputted the photodetector during at least one revolution of the rotating polygon mirror, wherein the computation unit determines a position in the height direction of the inspection object to determine an appearance positional coordinate of the inspection object based on the photoelectric conversion signal output stored in the data storage unit, and to perform the appearance inspection of the inspection object.

5. An appearance inspection method comprising:

rotating a rotating polygon mirror, which has at least three mirror surfaces in an outer peripheral portion and is configured such that mirror surface angles thereof formed by an rotation axis thereof and the mirror surfaces differ from one another in the mirror surfaces, about the rotation axis at a constant angular speed to linearly scan a light flux in a main scanning direction while the light flux is deflected toward an inspection object, the light flux being emitted from a light source to the mirror surface;

moving a collecting point in an inspection range in a height direction orthogonal to the main scanning direction of the inspection object while the light flux is collected at the collecting point using a collecting point position forming optical system in the deflection and scanning which are performed with the light flux by each of the mirror surfaces of the rotating polygon mirror;

moving the inspection object in a sub-scanning direction such that the collecting point is linearly scanned in the height direction of the inspection object, the collecting point being shifted in the sub-scanning direction orthogonal to the main scanning direction and the height direction by each of the mirror surfaces having different angles;

performing photoelectric conversion of light intensity of reflected light, reflected by the inspection object moved in the sub-scanning direction and deflected by the mirror surface of the rotating polygon mirror through the collecting point position forming optical system, into a photoelectric conversion signal output, the light intensity of the light flux depending on a distance between the collecting point and the reflection point of the light flux on the inspection object;

performing appearance inspection of the inspection object by determining an appearance positional coordinate of the inspection object based on the photoelectric conversion signal output;

moving the inspection object in the sub-scanning direction before further one revolution of the rotating polygon mirror at the constant angular speed is started; and performing the appearance inspection at a portion different from a portion to which the appearance inspection is already performed during one revolution of the rotating polygon mirror on the inspection object by the linear scanning of the collecting point in the main scanning direction and the movement of the collecting point in the height direction in the inspection range.

6. The appearance inspection method according to claim 5, wherein, in the deflection and scanning, the light flux, deflected and scanned by each of the mirror surfaces of the rotating polygon mirror, is collected at the collecting point by a scanning collective lens which constitutes the collecting point position forming optical system and of which an optical axis is arranged to be inclined with respect to a direction orthogonal to the rotation axis of the rotating polygon mirror, and the collecting point is collected so as to move in the inspection range in the height direction while linearly moved in the main scanning direction.

7. The appearance inspection method according to claim 5, wherein, in the deflection and scanning, the light flux, deflected and scanned by each of the mirror surfaces of the rotating polygon mirror, is collected at the collecting point by a scanning collective lens which constitutes the collecting point position forming optical system and of which an optical axis is arranged to be parallel to a direction orthogonal to the rotation axis of the rotating polygon mirror; and the light flux passing through the scanning collective lens is incident from an incident plane of a prism and is deflected to be outputted from an outgoing plane of the prism, and the collecting point is collected so as to move in the inspection range in the height direction while linearly moved in the main scanning direction, by the prism which constitutes the collecting point position forming optical system and is arranged between the scanning collective lens and the inspection object such that the incident plane and the outgoing plane are parallel to the main scanning direction.

* * * * *